(12) United States Patent
Rogan

(10) Patent No.: US 8,527,207 B2
(45) Date of Patent: Sep. 3, 2013

(54) ACCURATE IDENTIFICATION OF ORGANISMS BASED ON INDIVIDUAL INFORMATION CONTENT

(76) Inventor: Peter K. Rogan, London, CA (US)

( * ) Notice: Subject to any disclaimer, the term of this patent is extended or adjusted under 35 U.S.C. 154(b) by 1358 days.

(21) Appl. No.: 12/152,610

(22) Filed: May 15, 2008

(65) Prior Publication Data

US 2008/0286797 A1 Nov. 20, 2008

Related U.S. Application Data

(60) Provisional application No. 60/930,230, filed on May 15, 2007.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................. 702/19; 702/22; 703/11; 703/12

(58) Field of Classification Search
None
See application file for complete search history.

(56) References Cited

U.S. PATENT DOCUMENTS

| | | | |
|---|---|---|---|
| 5,426,027 A | 6/1995 | Lott et al. | |
| 5,547,835 A | 8/1996 | Koster | |
| 5,622,824 A | 4/1997 | Koster | |
| 5,691,141 A | 11/1997 | Koster | |
| 5,849,492 A | 12/1998 | Rogan | |
| 5,851,765 A | 12/1998 | Koster | |
| 5,867,402 A * | 2/1999 | Schneider et al. | 702/20 |
| 5,872,003 A | 2/1999 | Koster | |
| 6,074,823 A | 6/2000 | Koster | |
| 6,140,053 A | 10/2000 | Koster | |
| 6,194,144 B1 | 2/2001 | Koster | |
| 6,225,450 B1 | 5/2001 | Koster | |
| 6,238,871 B1 | 5/2001 | Koster | |
| 6,268,131 B1 | 7/2001 | Kang et al. | |
| 7,108,974 B2 | 9/2006 | Ecker et al. | |
| 7,217,510 B2 | 5/2007 | Ecker et al. | |
| 7,226,739 B2 | 6/2007 | Ecker et al. | |

(Continued)

OTHER PUBLICATIONS

Baldwin et al. Nuclear rDNA Evidence for Major Lineages of Helenioid Heliantheae (Compositae); Systematic Botany, 2002, vol. 27(1). p. 161-198.

(Continued)

*Primary Examiner* — Larry D Riggs, II
(74) *Attorney, Agent, or Firm* — Lathrop & Gage LLP

(57) ABSTRACT

An improved method for specific identification of any organisms by DNA hybridization or amplification is disclosed. Oligonucleotides are designed based on information analysis of sequences from a large number of related species. Oligonucleotide sequences that have the maximal specificity to certain nucleic acids from a particular species (or set of species) or type strain are selected for hybridization or amplification using DNA from the target organism. The presence or absence of a PCR or hybridization product may be used to identify the target organism. The resulting PCR products may also be compared with a DNA sequence database to obtain the identity of the organisms. The methods may prove useful in areas where rapid and accurate identification of an organism is desirable, such as in a hospital where identification of infectious agents may be critical, in the ethanol or beer industry where certain bacteria may be detrimental to the manufacturing process, or in the porcine industry where identification of different type strains of the porcine reproductive and respiratory syndrome virus (PRRV) is important for disease prevention.

20 Claims, 27 Drawing Sheets

(56) References Cited

U.S. PATENT DOCUMENTS

| | | |
|---|---|---|
| 7,255,992 B2 | 8/2007 | Ecker et al. |
| 2004/0161770 A1 | 8/2004 | Ecker et al. |
| 2004/0209260 A1 | 10/2004 | Ecker et al. |
| 2004/0219517 A1 | 11/2004 | Ecker et al. |
| 2005/0130196 A1 | 6/2005 | Hofstadler |
| 2005/0164215 A1 | 7/2005 | Hofstadler |
| 2005/0266397 A1 | 12/2005 | Ecker et al. |
| 2005/0270191 A1 | 12/2005 | Hofstadler |
| 2006/0121520 A1 | 6/2006 | Ecker et al. |
| 2006/0205040 A1 | 9/2006 | Sampath et al. |
| 2006/0240412 A1 | 10/2006 | Hall |
| 2006/0259249 A1 | 11/2006 | Sampath et al. |
| 2006/0275749 A1 | 12/2006 | Sampath et al. |
| 2006/0275788 A1 | 12/2006 | Ecker et al. |
| 2007/0264639 A1 | 11/2007 | Zenser et al. |

OTHER PUBLICATIONS

Schilling, E.E., et al. A revised classification of subtribe Helianthinae (Asteraceae: Heliantheae). I. Basal lineages, Botanical Journal of the Linnean Society, 2002, vol. 140, pp. 65-76.

Lowe T., et al., A computer program for selection of oligonucleotide primers for polymerase chain reactions, Nucleic acid research, 1990, vol. 18(7), pp. 1757-1761.

U.S. Appl. No. 12/058,353, Office Action dated Oct. 7, 2009, 13 pages.

U.S. Appl. No. 12/058,353, Search Reports cited in Office Action dated Oct. 7, 2009, 13 pages.

U.S. Appl. No. 12/058,353, Response to Office Action filed Feb. 8, 2010, 13 pages.

Aceto, S., et al.; Phylogeny and evolution of *Orchis* and allied genera based on ITS DNA variation: morphological gaps and molecular continuity; Mol Phylogenet Evol., Oct. 1999;13(1); pp. 67-76.

Ainouche, M.L. & Bayer, R.J. "On the origins of the tetraploid *Bromus* species (section *Bromus*, Poaceae): insights from internal transcribed spacer sequences of nuclear ribosomal DNA" Genome, Oct. 1997; 40(5); pp. 730-743.

Bains, W. "DNA Sequencing by Mass Spectrometry. Outline of a Potential Future Application" Chimicaoggi. vol. 9, No. 10, Oct. 1991; pp. 13-16, 1991.

Binns, S.E., et al "A taxonomic revision of *Echinacea* (Asteraceae: Heliantheae)" Syst. Bot. 2002, vol. 27, pp. 610-632.

Bobowski, B.R., et al. "Identification of roots of woody species using polymerase chain reaction (PCR) and restriction fragment length polymorphism (RFLP) analysis" Mol Ecol. Mar. 1999; 8(3); pp. 485-491.

Chen, C.H. Winston, et al.; Laser Desorption Mass Spectrometry for Fast DNA Sequencing; U.S. Department of Energy, DOE Human Genome Program Contractor-Grantee Workshop IV, 1994; retrieved from http://www.oml.gov/sci/techresources/Human_Genome/publicat/94SANTA/sequencing/chen.shtml.

Chen, C.H. Winston, et al.; Laser Desorption Mass Spectrometry for DNA Sequencing and Analysis; Session K14—Nucleic Acids; MIXED session, Tuesday afternoon, Mar. 17, 1998, Los Angeles Convention Center; retrieved from http://flux.aps.org/meetings/YR98/BAPSMAR98/abs/S2000012.html.

Chen, C.H., et al.; Laser Desorption Mass Spectrometry for high throughput DNA analysis and its applications; 1999; retrieved from http://www.osti.gov/bridge/servlets/purl/3655-nx94bv/webviewable/3655.pdf.

Chen, C.H. Winston, et al.; Laser Desorption Mass Spectrometry for DNA Sequencing and Analysis; DOE Human Genome Program Contractor-Grentee Workshop VIII Jan. 12-16, 1999 Oakland, CA; retrieved from http://www.ornl.gov/sci/techresources/Human_Genome/publicat/99santa/45.html.

Chen, C.H. Winston, et al.; Laser mass sepctrometry for DNA sequencing, disease diagnosis, and fingerprinting; SPIE vol. 2985; 1997; pp. 70-81.

Emshwiller, E. & Doyle, J.J.; Origins of domestication and polyploidy in oca (*Oxalis tuberose*: Oxalidaceae). 2. Chloroplast expressed glutamine synthetase data. American Journal of Botany 89(7), 2002; pp. 1042-1056.

Emshwiller, E. & Doyle, J.J; Origins of domestication and polyploidy in oca (*Oxalis tuberosa*: Oxalidaceae): nrDNA ITS data. American Journal of Botany 85(7); 1998; pp. 975-985.

Ecker, D.J., et al. "Rapid identification and strain-typing of respiratory pathogens for epidemic surveillance" Proc Natl Acad Sci USA 102(22); May 2005, pp. 8012-8017.

Ecker, D.J., et al. "The Microbial Rosetta Stone Database: a compilation of global and emerging infectious microorganisms and bioterrorist threat agents" BMC Microbio15(1):19, (2005); 17 pages.

Ecker, J.A., et al. "Identification of *Acinetobacter* species and genotyping of *Acinetobacter baumannii* by multilocus PCR and mass spectrometry" J Clin Microbio144(8), (2006), pp. 2921-2932.

Edwards, J.R., et al; Mass-Spectrometry DNA Sequencing; Mutation Research 573 (2005) 3-12.

Edwards, J.R. et al.; DNA sequencing using biotinylated dideoxynucleotides and mass spectrometry; Nucleic Acids Research 2001, vol. 69, No. 21, e104; pp. 1-6.

Fitzgerald, M.C. et al; The Analysis of Mock DNA Sequencing Reactions Using Matrix-assisted Laser Desorption/Ionization Mass Spectrometry; Rapid Communications in Mass Spectrometry, vol. 7; 895-897 (1993).

Francisco-Ortega J., et al., Internal Transcribed Spacer Sequence Phylogeny of *Crambe* L. (Brassicaceae): Molecular Data Reveal Two Old World Disjunctions; Mol Phylogenet Evol., Apr. 1999; 11(3); pp. 361-380.

Hall, T.A. et al.; Base composition analysis of human mitochondrial DNA using electrospray ionization mass spectrometry: a novel tool for the identification and differentiation of humans; Analytical Biochem. 344 (2005); pp. 53-69.

Herwig, R., et al.; Information theoretical probe selection for hybridisation experiments; vol. 16, No. 10, 2000, pp. 890-898.

Hujer, K.M. et al. "Analysis of antibiotic resistance genes in multidrug-resistant *Acinetobacter* sp. isolates from military and civilian patients treated at the WalterReed Army Medical Center" Antimicrob Agents Chemother 50(12), (2006), pp. 114-123.

Jacobson, K.B. et al.; Applications of mass spectrometry to DNA sequencing; GATA 8(8), 1991; pp. 223-229.

Jupe, E.R. & Zimmer, E.A.; Unmethylated regions in the intergenic spacer of maize and teosinte ribosomol RNA genes; Plant Mol Biol.; Mar. 1990;14(3); pp. 333-347.

Kirpekar, F., et al.; DNA sequence analysis my MALDI mass spectrometry; Nucleic Acids Research, 1998, vol. 26, No. 11; pp. 2554-2559.

Kim, D.H. et al.; Genetic diversity of *Echinacea* species based upon amplified fragment length polymorphism markers. Genome, Feb. 2004; 47(1); pp. 102-111.

Koopman, W.J.M., et al., Phylogenetic Relationships Among *Lactuca* (Asteraceae) Species and Related Genera Based on ITS-1 DNA Sequences; Am. J. Bot. 85(11), 1998; pp. 1517-1530.

Koster, H. et al.; A strategy for rapid and efficient DNA sequencing by mass spectrometry; Nature Biotech; vol. 14, Sep. 1996; pp. 1123-1128.

Krause, J. et al.; High Resolution Characterization of DNA Fragment Ions Produced by Ultraviolet Matrix-Assisted Laser Desorption/Ionization Using Linear and Reflecting Time-of-Flight Mass Spectrometry; J. Am. Soc. Mass Spectrum., 1999, 10, pp. 423-429.

Lesnik et al. (2005) "Identification of conserved regulatory RNA structures in prokaryotic metabolic pathway genes" Biosystems 80(2):145-54.

Little, D.P., et al.; Rapid Sequencing of Oligonucleotides by High-Resolution Mass Spectrometry; J. Am Chem Soc. 116, 1994, pp. 4893-4897.

Little, D.P. & McLafferty, F.W.; Sequencing 50-mer DNAs Using Electrospray Tandem Mass Spectrometry and Complementary Fragmentation Methods; J. Am Chem Soc. 117, 1995, pp. 6783-6784.

Little, D.P., et al.; Sequencing Information from 42-108-mer DNAs (Complete for a 50-mer) by Tandem Mass Spectrometry; J. Am Chem Soc. 118, 1996, pp. 9352-9359.

Little, D.P., et al.; Verification of 50- 100-mer DNA and RNA sequences with high resolution mass spectrometry; Proc. Natl. Acad. Sci. USA vol. 92, Mar. 1995, pp. 2318-2322.

Liu, J.-S. & Schardl, C.L.; A conserved sequence in internal transcribed spacer 1 of plant nuclear rRNA genes; Plant Mol Biol., Oct. 1994 vol. 26, No. 2, pp. 775-778.

Martin, W.J.; New technologies for large-genome sequencing; Genome vol. 31, 1989; pp. 1073-1080.

Murray, K.K.; Special Feature: Tutorial—DNA Sequencing by Mass Spectrometry; Journal of Mass Spectrometry; vol. 31, 1996; pp. 1203-1215.

Nelson, R.W., et al.; Volitization of High Molecular Weight DNA by Pulsed Laser Ablation of Frozen Aqueous Solutions; Science vol. 246; Dec. 1989; pp. 1585-1587.

Ni, J. et al.; "Interpretation of Oligonucleotide Mass Spectra for Determination of Sequence Using Electrospray Ionization and Tandem Mass Spectrometry"; Anal. Chem 1996, vol. 68, No. 13; pp. 1989-1999.

Nordhoff, E. et al.; Direct Mass Spectrometric Sequencing of Low-picomole Amounts of Oligodeoxynucleotides with up to 21 Bases by Matrix-assisted Laser Desorption/Ionization Mass Spectrometry; Journal of Mass Spectrometry; vol. 30 (1995); pp. 99-112.

Parr, G.R., et al; "Matrix-Assisted Laser Desorption/Ionization Mass Spectrometry of Synthetic Oligodeoxyribonucleotides", Rapid Communications in Mass Spectrometry, 1992, 6, 369-372.

Reamon-Buttner, S.M., et al., AFLPs represent highly repetitive sequences in *Asparagus officinalis* L. C. Chromosome Res.; 1999, vol. 7 No. 4; pp. 297-304.

Rogan P.K., et al.; Visual Display of Sequence Conservation as an Aid to Taxonomic Classification Using PCR Amplification; In: Visualizing Biological Information, CA Pickover (ed). World Scientific, River Edge NJ, 1995; pp. 21-32.

Roskey, M.T., et al.; DNA sequencing by delayed extraction-matrix-assisted laser desorption/ionization time of flight mass spectrometry; Proc Natl. Acad. Sci. USA, vol. 93, May 1996, pp. 4724-4729.

Sakai, R.K., et al.; Enzymatic amplification of beta-globin genomic sequences and restriction site analysis for diagnosis of sickle cell anemia; Science 20; Dec. 1985; pp. 1350-1354.

Sampath, R. et al. (2005) Rapid identification of emerging Infectious agents Using PCR and Electrospray Ionization Mass Spectrometry; Ann. N.Y. Acad. Sci. 1102 (2007); pp. 109-120.

Sampath, R. et al. "Rapid identification of emerging pathogens: coronavirus" Emerg Infect Dis (2005) 11(3): 373-9.

Sanger F, et al. "DNA sequencing with chain-terminating inhibitors." Proc Natl Acad Sci U S A. 1977 74 (12); pp. 5463-5467.

Schneider, T.D. & Stephens, R.M.; Sequence logos: a new way to display consensus sequences; Nucleic Acids Research; vol. 18, No. 20, 1990, pp. 6097-6100.

Schneider, T.D., et al.; Information Content of Binding Sites on Nucleotide Sequences; J. Mol. Biol. (1986) 188; pp. 415-431.

Seth, P.P.; et al; Discovery of a New Class of RNA-Binding Small Molecules for the Hepatitis C Virus: Internal Ribosome Entry Site IIA Subdomain; J. Med. Chem. 48 (2005); pp. 7099-7102.

Siudzak, G. "The emergence of mass spectrometry in biochemical research" Proc. Natl Acad Sci USA, vol. 91, Nov. 1994, pp. 11290-11297.

Skinner, K.A.; Bacterial contaminants of fuel ethanol production; J. Ind. Microbial. Biotechnol. vol. 31, 2004; pp. 401-408.

Soltis, P.S. & Soltis, D.E.; The role of genetic and genomic attributes in the success of polyploids Proc Natl Acad Sci USA, Jun. 2000; 97(13); pp. 7051-7057.

Stimpel, M., et al.; Macrophage Activation and Induction of Macrophage Cytotoxicity by Purified Polysaccharide Fractions from the Plant *Echinecea purpurea*; Infection and Immunity, vol. 46, No. 3, Dec. 1984; pp. 845-849.

Tang, K., et al., Mass-Spectrometry of Laser-Desorbed Oligonucleotides. Rapid Communications in Mass Spectrometry, 1992. 6(6): p. 365-368.

Tang, W., et al.; Controlling DNA Fragmentation in MALDI-MS by Chemical Modification; Anal. Chem., vol. 69, 1997, pp. 302-312.

Tang K, et al.; Matrix-assisted laser desorption/ionization mass spectrometry of immobilized duplex DNA probes. Nucleic Acids Res. Aug. 25, 1995; 23(16); pp. 3126-3131.

Tooley, P.W., et al.; Phylogenetic Inference Based on Information Theory-Based PCR Amplification; J. Phytopathology, vol. 146; (1998) pp. 427-430.

Van Der Stappen, J., et al.; Sequencing of the Internal transcribed spacer region ITS1 as a molecular tool detecting variation in the *Stylosanthes gulanenis* species complex; Theor. Appl. Genet. 96, 1998, pp. 869-877.

Van Ert et al. (2004) "Mass spectrometry provides accurate characterization of two genetic marker types in *Bacillus anthracis*" Biotechnigues 37(4):642-4.

Whiting, M., et al.; Detection of *Pediococcus* spp.in Brewing Yeast by a Rapid Immunoassy; Appl. Environ. Microbial., vol. 58, No. 2, Feb. 1992; pp. 713-716.

Woese, C.R.; Bacterial Evolution; Microbial Rev. Jun. 1987 51(2); pp. 221-271.

Wu, K.J., et al.; Time-of-Flight Mass Spectrometry of Underivatized Single-Stranded DNA Oligomers by Matrix-Assisted Laser Desorption, Anal. Chem., 1994, pp. 1637-1645.

Maxam, A.M. & Gilbert, W., "Sequencing end-labeled DNA with base-specific chemical cleavages." Methods Enzymol.; ed. Grossman & Moldave; 1980 vol. 65(1):499-560.

* cited by examiner

FIG. 3

```
bits (window)      number of sites(+), Gaussian distribution(:)

<12.46016         1    +    ←———— Most divergent sequence
  13.23620         2    ++
  14.01225         2    ++
  14.78829         0    :
  15.56434         0    :
  16.34038         0    :
  17.11643         5    +*+++
  17.89247         0     :
  18.66852         5    ++*++
  19.44456         0       :
  20.22061         5    +++*+
  20.99665         2    ++   :
  21.77270         2    ++    :
  22.54874         4    ++++  :
  23.32479         4    ++++ :
  24.10083         2    ++    :
  24.87688         9    +++++*+++
  25.65292         0         :
  26.42897         7    +++++*+
  27.20501        38    ++++*++++++++++++++++++++++++++++++++++
  27.98106         1    +  :  ←———— "Consensus sequence"
```

FIG. 4

| Accession | Sequence | $R_i$ (bits) | SEQ ID NO |
|---|---|---|---|
| Low information content: | | | |
| U03040 | aacagcggctcaaatttacagct | 12.46 | 1 |
| U64929 | aacagcagctcccaattgcagtc | 14.10 | 2 |
| AF020048 | gacagcagctcccatctacagct | 14.36 | 3 |
| AF339499 | aacaacagctcccatctacagct | 17.11 | 4 |
| High information content: | | | |
| U66383 | agcagcagctctcattttcagtt | 26.88 | 5 |
| AF171682 | acgctctgttttggttttccact | 27.25 | 6 |
| U66386 | aacagcagctctcattttcagtt | 27.50 | 7 |
| X92942 | acgctatgttttggttttccatt | 27.88 | 8 |
| AF171673 | acgctatgctttggttttccatt | 27.98 | 9 |

FIG. 5

| $R_{sequence}$/bp window ≤ bits | No. sites | |
|---|---|---|
| 0.00000 | 4766 | ++++++++++++++++++++++++++++++++++++++++++++++++++ |
| 0.05783 | 819 | +++++++++:. |
| 0.14039 | 1615 | +++++++++++*+++++++ |
| 0.22294 | 871 | +++++++++++ |
| 0.30549 | 602 | ++++++++ |
| 0.38804 | 790 | ++++++++++ |
| 0.47060 | 1337 | +++++++++++++++++ |
| 0.55315 | 1270 | ++++++++++++++++ |
| 0.63570 | 1007 | +++++++++++++ |
| 0.71826 | 1244 | ++++++++++++++++ |
| 0.80081 | 1296 | +++++++++++++++++ |
| 0.88336 | 1512 | +++++++++++++++++++ |
| 0.96592 | 1772 | +++++++++++*+++++++++++ |
| 1.04847 | 1830 | ++++++++++*+++++++++++++ |
| 1.13102 | 1622 | +++++++++++++++++++++ |
| 1.21357 | 1261 | ++++++++++*++++++ |
| 1.29613 | 824 | +++++*++++ |

$R_{sequence}$/bp = 0.68

FIG. 7

| Species | (extended) AccuAmp Sequence | Length (of AccuAmp sequence) | Position (in multiple alignment) | Position (in original seq) | Tm (°C) | Primer sequences derived from AccuAmp sequence a (Forward (F), Reverse (R)) Number in parenthesis indicates SEQ ID. No | Frequency |
|---|---|---|---|---|---|---|---|
| L.acidophilus | tgacgttggga aacgctagcgg (SEQ ID No. 10) | 22 | 329 | (120) | 59.8<br>60.8<br>59.8 | TGACGTTGGGAAACGCTAG (F)(11)<br>GACGTTGGGAAACGCTAGC (F)(12)<br>CTAGCGTTTCCCAACGTCA (R)(13) | *, unique in all 16s db |
| L.brevis1 | (caaaat) ccg catgatttt( gttt) (SEQ ID No. 14) | 12 | 593 | (220) | 59.3<br>59.3<br>59.3 | AAAATCCGCATGGATTTTGT (F)(15)<br>AAATCCGCATGGATTTTGTT (F)(16)<br>AAACAAAATCCATGCGGATT (R)(17) | Unique in all 16s db (4 strains) |
| L.brevis^ | Tcccgggcgt Attagttag (SEQ ID No. 18) | 20 | 811 | (277) | 60.6<br>62.3<br>60.6 | CCCGCGGCGTATTAGTTAG (F)(19)<br>CTAACTAATACGCCGCGGGA (R)(20)<br>CTAACTAATACGCCGCGGG (R)(21) | *, unique in all 16s db (4 strains) |
| Ped.damnosus | (tctg) gtctt gtaactgacg( ctga) (SEQ ID No. 22) | 15 | 1759 | (767) | 57.5<br>56.5<br>56.5 | TGGTCTTGTAACTGACGCTG (F)(23)<br>CGTCTTGTAACTGACGCTGA (F)(24)<br>TCAGCGTCAGTTACAAGACC (R)(25) | *, unique in all 16s db (2 strains) |
| Ped.parvulus | (ctata) aagt gagtggcca (a cggg) (SEQ ID No. 26) | 13 | 345 | (83) | 56.5<br>60.1<br>51.5<br>60.1 | TATAAAGTGAGTGGCGAACG (F)(27)<br>ATAAAGTGAGTGGCGAACGG (F)(28)<br>CTATAAAGTGAGTGGCGAA (F)(29)<br>CCGTTCGCCACTCACTTTAT (R)(30) | *, 15 hits in all 16s db including other species |
| S. cerevisiae | HMR flank | 21<br>22 | Gb: X00808 | 262-282<br>476-455 | 60.2<br>60.3 | CCAACATTTTGTATATGCCG (F)(31)<br>TCCAACACATTTAGGAAAAAACGC (R)(32) | PCR product: 215 bp,25% G/C |

* Unique in 16S rRNA type strain database
^ L.brevis1 and L.brevis are two different strains of Lactobacillus brevis in the type strain database.

FIG. 10

ACCURATE IDENTIFICATION OF ORGANISMS BASED ON INDIVIDUAL INFORMATION CONTENT

RELATED APPLICATIONS

This application claims priority of U.S. Provisional Application No. 60/930,230 filed on May 15, 2007, the contents of which is hereby incorporated into this application by reference.

SEQUENCE LISTING

This application is accompanied by a sequence listing in a computer readable form that accurately reproduces the sequences described herein.

BACKGROUND

1. Field of the Invention

The present disclosure pertains to the use of DNA for rapid detection and identification of an organism. More particularly, the disclosure relates to a methodology based upon information theory for identification of an organism by utilizing unique nucleic acid features present in the genome or transcriptome of that organism.

2. Description of Related Art

Oligonucleotides are widely used in molecular biology for DNA amplification, or hybridization, among other applications. Oligonucleotides suitable for amplification of or hybridization with a target DNA or RNA sequence (the "target sequence") may be selected by visual inspection of the target sequence. Mathematical algorithms or computer software may also be used to help select an "optimal" oligonucleotide. The extent to which an oligonucleotide binds to a DNA or RNA segment depends on the sequence similarity between the oligonucleotide and the target sequence.

In practice, the number of oligonucleotide molecules that specifically bind to a target DNA sequence but not to other sequences depend not only on the sequence similarity between the oligonucleotide and the target sequence, but also on the sequence similarity between the oligonucleotide and those other sequences in the background (the "noise" or the "background" DNA). These noise DNA may be on the same molecule as the target DNA or they can be on different molecules. If an oligonucleotide binds equally well to the background DNA and the target DNA, it can not effectively distinguish between the target DNA and the background DNA. Thus, in order to design oligonucleotides that are truly specific to a target DNA, sequence variations between the target DNA and background DNA shall be taken into consideration. No methods have been reported which quantitatively calibrate sequence variations among different DNA fragments in order to design an "optimal" oligonucleotide that specifically binds to the target DNA.

Specific recognition of a target DNA by oligonucleotides may be desirable in many applications. For instance, different strains of pathogenic agent may react differently to the same treatment. It is sometimes critical to rapidly obtain the exact identity of the strain. Because some strains may be morphologically indistinguishable from other strains, molecular characterization, such as DNA polymerase chain reaction (PCR), may be required for their identification. However, certain strains may differ from other strains only in a few nucleotides, and conventional PCR may not be adequate for their specific identification. Under those circumstances, it is important that the primers and the condition be optimized for a target DNA such that a positive PCR or hybridization result may unambiguously indicate the presence of a particular strain.

Another instance where highly specific recognition of a target DNA by an oligonucleotide is desirable is in the detection of beer-spoilage bacteria. In the beer industry, prevention of beer-spoilage by contaminating microorganisms is a major concern of commercial breweries. The predominant organisms which have been shown to spoil beer, or which have been associated with beer-spoilage are members of the genera *Lactobacillus, Pediococcus, Pectinatus*, and *Megasphaer* (see, e.g., The Prokaryotes, Vol, II, 2nd Edition, Balows, et al, Eds., 1991; Hardwick, W. A., Ed. (1995). Handbook of Brewing. Marcel Dekker, Inc., New York; and Priest, F. G., and Campbell, I., Eds. (1987). Brewing Microbiology. Elsevier Applied Science, London).

Several studies have identified bacterial strains capable of spoiling beer, and the relative numbers of strains within the species so implicated were, in decreasing order of importance: *Lactobacillus brevis, P. damnosus, L. casei, L. lindneri, L. coryniformis, L. buchneri, L. plantarum*, and *L. curvatus*. Although these various strains are all capable of spoiling beer, they represent a diverse group of microorganisms. It may be desirable to specifically identify the beer spoilage strain so that preventive and remedial measures may be taken.

Members of the genus *Pediococcus* are Gram-positive cocci and frequently form tetrads. They have complex nutritional requirements and are capable of fermenting a variety of sugars. They are facultative anaerobes found in a variety of habitats, most frequently associated with fermenting vegetation. There are eight known species in this genus; *P. damnosus* is the primary member of the genus known to cause beer spoilage. See U.S. Pat. No. 5,484,909.

The genus *Lactobacillus* is Gram-positive nonsporulating rod shaped organism. Organisms of this genus typically utilize strictly fermentative metabolism and have complex nutritional requirements. They may be found in a variety of habitats, including water, dairy, meat and fish products, vegetation and fermenting vegetation, and in the mouth and intestinal tract of mammals.

Conventional methods used in breweries to detect beer spoilage bacteria involve plating, cultivation in liquid broths, followed by microscopy and staining in combination with enzymatic tests such as catalase for typing of the contaminants. These procedures are well established, but their main disadvantage is the long wait before the contaminating species may be identified. Moreover, the information gathered from conventional tests is very limited, which usually does not allow accurate identification of the contaminant species. The limited information regarding the contaminants hinders rapid and accurate tracing of the source of the contamination or a thorough hygiene monitoring.

Other methods have been developed using modern biology tools to detect and identify the bacteria species. For instance, direct fluorescence antibodies have been used to identify and classify the beer spoilage microorganisms. See, e.g., Whiting, M., Crichlow, M., Ingledew, W. M., and Ziola, B. Detection of *Pediococcus* spp. in brewing yeast by a rapid immunoassay. Appl. Environ. Microbiol. 58(2):713-716, 1992; Nucleic acid probes for DNA hybridization and primers for PCR have also been employed for culture confirmation. See M. Kiehne et al., Detection and Identification of Beer-Spoilage Bacteria Using Real-Time Polymerase Chain Reaction, Master Brewers Association of the Americas TQ, 2005, 42: 214-8. Although these new reports have addressed some of the contamination problems plaguing the brewing industry, their application is limited because they can not precisely identify a particular strain if there are other strains with similar DNA sequence in the background.

Another area where bacteria contamination is a major concern is the rapidly growing ethanol industry. Microorganisms such as yeast are frequently used to convert biomaterials such as corn, grass, or wood chips to ethanol. During the manufacturing of ethanol, bacteria contamination can occur in almost every step of the process. The biomaterials may bring bacteria from the field into the fermentation system. In addition, bacteria contamination may be found in yeast propagators, steep tanks, fermentors and heat exchangers, where the temperature, pH and glucose levels are ideal for bacteria growth. For some ethanol plants, controlling gram-positive bacteria is a continuous battle. See e.g., Kelly A., Skinner and Timothy D. Leathers, Bacterial contaminants of fuel ethanol production. Journal of Industrial Microbiology and Biotechnology, Volume 31, Number 9/October 2004.

To minimize bacteria contamination, most ethanol plants clean the equipments on a regular basis and run their processes at low pH levels. Many plants also try to perform their steeping, mashing and fermentation as quickly as possible to minimize lactic acid formation. Unfortunately, even low levels of bacteria reduce ethanol yield and, in the most severe cases, can slow or stop fermentation. Thus, it is desirable to monitor the presence of and accurately identify these bacteria in the ethanol industry.

Yet another example where highly specific recognition of a target DNA by an oligonucleotide is desirable is in the detection of porcine reproductive and respiratory syndrome virus (PRRV). PRRV may cause infertility and preweaning mortality of the infected pigs and may thus cause significant production losses in the porcine industry. PRRV has a genome with 13-15 kb single strand RNA. It has been estimated that about 60-80% of swine herds in the U.S. may carry the virus. One of the hallmarks of PRRV is that it contains numerous strains which differ from one another in the highly polymorphic envelope gene. As a result, one vaccine derived from one strain may not be effective against other strains. Current methods to detect PRRV infection use ELISA assays. However, ELISA requires fresh chilled tissue and does not discriminate between different strains.

SUMMARY

It is hereby disclosed a methodology by which nucleic acid technology is employed to identify an organism (also referred to as a "target organism") without culturing cells. The disclosed method contrasts with traditional sequence analysis which requires visual inspection of a multiply aligned set of related sequences to select the sequences of oligonucleotides for hybridization or PCR of a particular target sequence. The disclosed method further differs from other sequence analysis methods which typically do not require quantitative comparison of different sequences. Individual information theory may provide a strictly computational metric which may utilize rank ordering of potential primer sequences to guide the selection of oligonucleotides that hybridize to or amplify only DNA from one organism but not DNA from others. This quantitative method may prove useful for selecting hybridization or PCR primers, thereby eliminating the need to perform visual inspection of the sequence alignments.

The methodology disclosed here is improved upon the technology described in U.S. Pat. No. 5,849,492, which is hereby incorporated by reference. Briefly, information content (in bits) may be used to precisely quantify both the similarities and divergence among DNA sequences. Sequence logos may be constructed from multiply aligned sequences based upon the information content. High and low average information content sequence windows may be located. Individual information contents of contributing sequences in low information content windows are ranked. Those sequences with the lowest individual information contents may be selected as sequence specific primers.

For purpose of this disclosure, the terms "average information" and "individual information" have distinct meanings. Average information (or average information content) is used to locate one or more segment or sequence window that has low overall conservation levels in the alignment of related sequences. After such a sequence window has been identified, individual information (or individual information content) of the segments within the window on individual related sequences are calculated and compared. Those segments that are usually found to be species-specific (or type-strain specific) are those with low individual information in that same sequence window that has been found to have low average information content. There may be several species- or type-strain specific primers with low individual information within the same sequence window, each detecting a different species or strain. However, because the aligned sequences have low average information, there are also individual sequences in the alignment which are well-conserved and have relatively higher levels of individual information. These sequences are generally not suitable for use as species-specific or type strain-specific oligonucleotide primers because they are more likely to resemble and exhibit hybridization properties found in other strains or species and may lead to non-specific hybridization or non-specific amplification.

Those sequences with low individual information may be selected for hybridization or amplification using DNA from the target organism. The presence or absence of a PCR or hybridization product may be used to indicate the presence or absence of the target organism. The resulting PCR products may also be compared with a DNA sequence database to obtain the identity of the organisms. In addition, quantitative methods such as quantitative PCR (qPCR) may also be used to determine the relative abundance of the target organism.

In one aspect, a method for identification of an organism may include the steps of (a) aligning a set of related sequences, said set of related sequences comprising more than one polynucleotide sequences, wherein at least one sequence of said more than one polynucleotide sequences is known to exist in said organism; (b) searching for a segment with low average information content from said set of aligned related sequences; and (c) selecting from said segment one or more sequences with low individual information contents or a portion thereof as oligonucleotides for identification of said organism. In a preferred embodiment, the search for the segment with low average information content is by locating high and low average information content sequence windows along the entire length of the polynucleotide molecule. The length of the sequence window is preferably in the range of 20-25 nucleotides.

In another aspect, the polynucleotide molecule is a DNA molecule, and preferably, a ribosomal DNA molecule. The oligonucleotides thus selected according to the method disclosed here may be used to hybridize with at least one DNA molecule obtained from said organism. In another aspect, the oligonucleotides may be used as specific primers for amplifying at least one DNA molecule obtained from an organism to identify the organism. Amplification may be achieved by, for example, polymerase chain reaction and/or ligase chain reaction.

In another aspect, the disclosed methods may be used to identify a species in a sample containing different species. Examples of the species include animal species, plant species or microorganisms. Microorganisms may include but are not limited to viruses, bacteria, yeast.

In yet another aspect, the disclosed methods may be used to identify a type strain among different type strains. Different type strains may all belong to the same species but nevertheless possess different phenotypes due to underlying genetic differences. In one embodiment, the organism to be identified is a porcine reproductive and respiratory syndrome virus (PRRV). More particularly, the disclosed method may be used to distinguish among different type strains of PRRV.

In another embodiment, the organism to be identified is an organism which negatively affects the production of ethanol from a biomaterial. An organism may negatively affect an industrial process if it reduce the total output, the rate of production and/or the quality of product being produced. For instance, a number of bacterial species, such as Lactobacillus brevis and Lactobacillus fermentum, are known to negatively affect ethanol production from biomaterials.

In another embodiment, the organism to be accurately identified by the present method is a bacterial species that negatively affects the fermentation process of a beverage. Examples of such beverages may include but are not limited to beer, wine and other liquors. In the case of beer production, a bacterium that negatively affects beer production is also known as a beer spoilage organism. The disclosed method may be used for quality control purposes in the manufacturing of various beverages that requires some form of fermentation.

In yet another aspect, the disclosed method may be useful when rapid and accurate identification of an infectious agent such as a bacterial species or a virus is desirable. Such instances may arise in a hospital or a clinic where a treatment plan relies on information regarding the identity of the infectious agent. Under those circumstances, the presently disclosed method may be used in conjunction with methods to identify a broad spectra of organisms such as those disclosed in U.S. Pat. No. 5,849,492 and U.S. patent application Ser. No. 12/011,425 filed Jan. 25, 2008, which is hereby incorporated into this disclosure by reference.

In yet another aspect, the disclosed method for accurate identification of an organism may include the steps of (a) aligning a first polynucleotide sequence known to exist in a first organism with at least one additional related polynucleotide sequence from at least one different organism, said at least one additional related polynucleotide sequence being different from one another and from said first polynucleotide sequence; (b) searching for a window with low average information content on said aligned sequences; and (c) selecting from said first polynucleotide sequence at least one segment with low individual information content or a portion thereof as an oligonucleotide for identification of said first organism.

The average information content may be determined by calculating the values of $R_{sequence}$ for every equal-length window on the aligned sequences. The $R_{sequence}$ values of all equal-length windows may then be compared to identify those with low average information content. Preferably, the selected segment with low individual information content has an $R_i$ value that is at least one standard deviation below the average information content of sequences within the same window on the aligned polynucleotide sequences demarcated by the boundaries of the selected segment.

In yet another aspect, a method for identification of a type strain is disclosed which may include the steps of (a) aligning a first polynucleotide sequence known to exist in a first type strain with at least one additional polynucleotide sequence from at least one different type strain, wherein said at least one additional polynucleotide sequence is different from one another and from said first polynucleotide sequence, and said first type strain and said at least one different type strain belong to the same species; (b) searching for a window with low average information content on said aligned sequences; and (c) selecting from said first polynucleotide sequence at least one segment with low individual information content or a portion thereof as an oligonucleotide for identification of said first type strain.

In another embodiment, the present disclosure provides oligonucleotide molecules that may be used as hybridization probes or PCR primers for identification of organisms of various species. These oligonucleotides may include, for example, oligonucleotide molecules of SEQ ID Nos 1-9, 11-13, 15-17, 19-21, 23-25 and 27-42. These oligonucleotides may be used alone or in combination, such as in primer pairs for specific amplification of DNA fragments from the target organism.

The methodology disclosed here may prove useful for automating diagnostic test development, and retrieval of particular genes among families of related sequences. Examples are also provided wherein the methodology may be applied precisely to identify beer spoilage bacteria and porcine reproductive and respiratory virus.

BRIEF DESCRIPTION OF THE DRAWINGS

Figure 3:
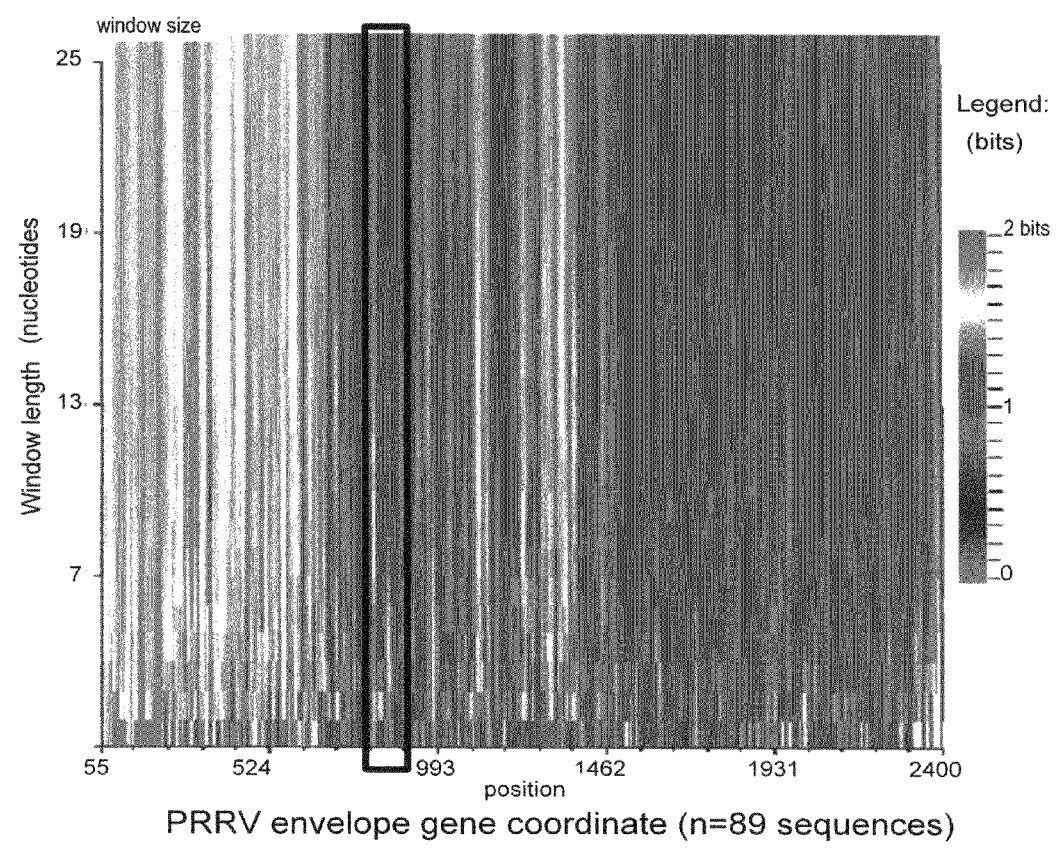

FIG. 3 shows a windowed information plot based on the calculated information content of each window throughout the entire segment shown in FIG. 1.

FIG. 4 shows the distribution of Ri values at position 770 of the sequence logo with a window length of 23 nucleotides.

FIG. 5 shows some examples of PRRV primer sequences with high or low information content at position 770 of the sequence logo and the GenBank accession number of the sequence from which they are derived.

FIG. 7 shows a histogram of $R_{sequence}$ per base pair values for 16S rDNA windows.

FIG. 10 summarizes some oligonucleotides selected for specific amplification of beer spoilage bacteria strains.

DETAILED DESCRIPTION

Figure 1:
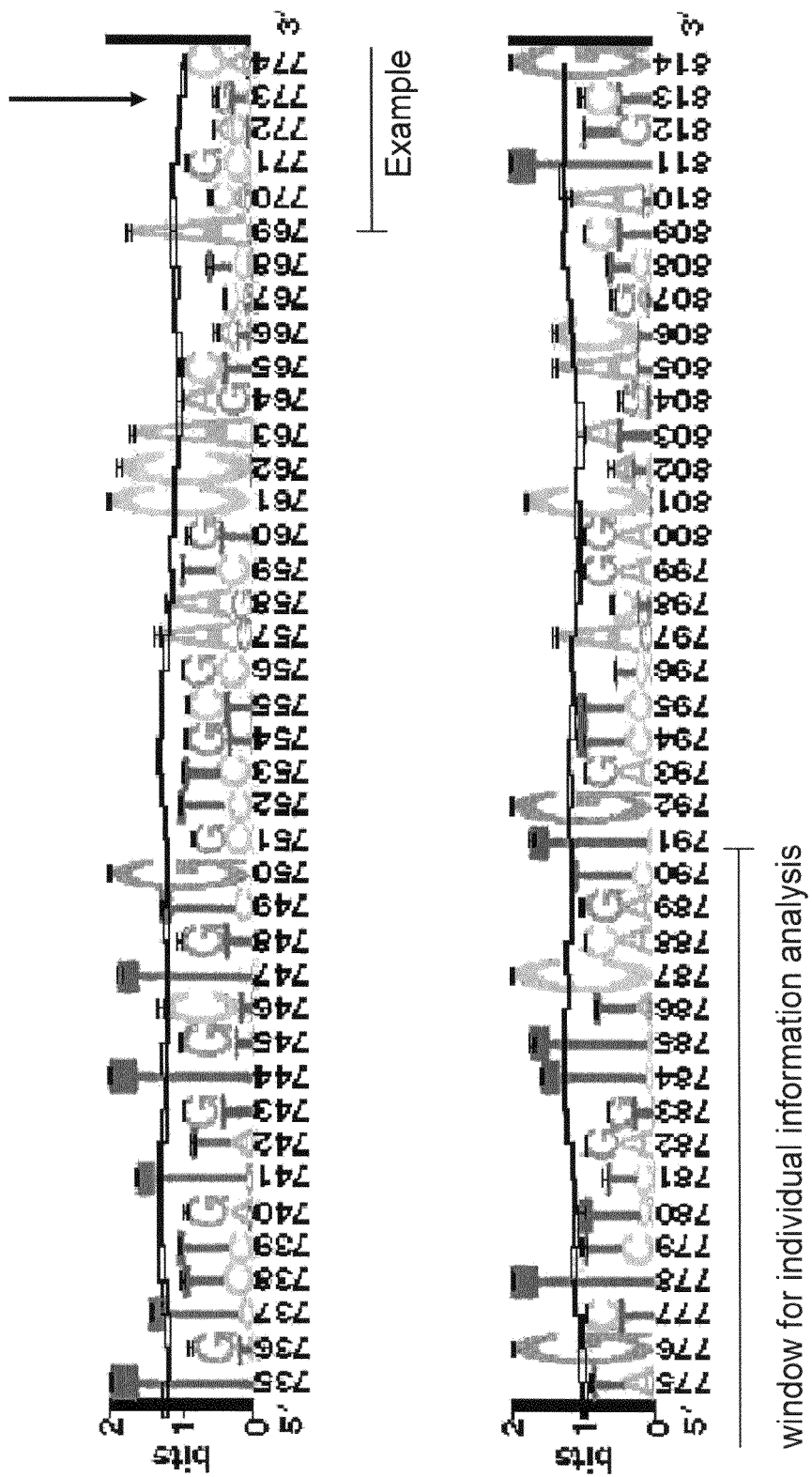
FIG. 1 shows a portion of the sequence logo of the entire envelope gene of PRRV containing the window used for designing oligonucleotides.
Figure 2:
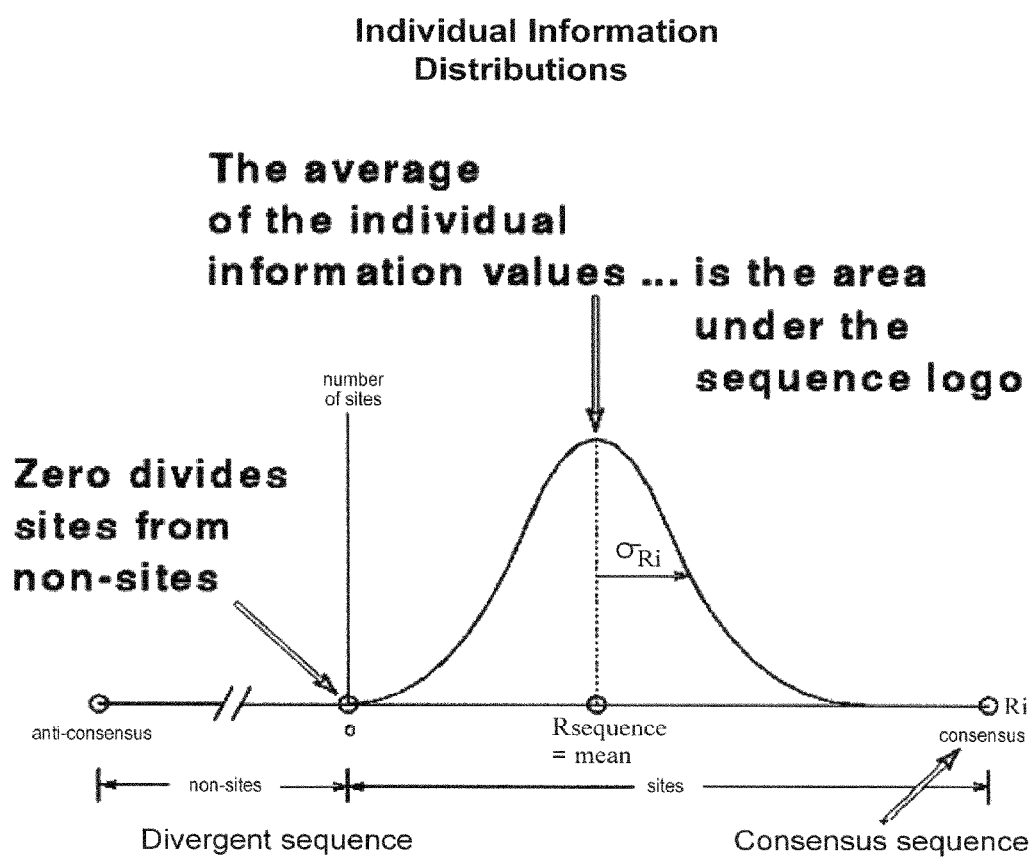
FIG. 2 shows the distribution of the average of the information values.
Figure 6:
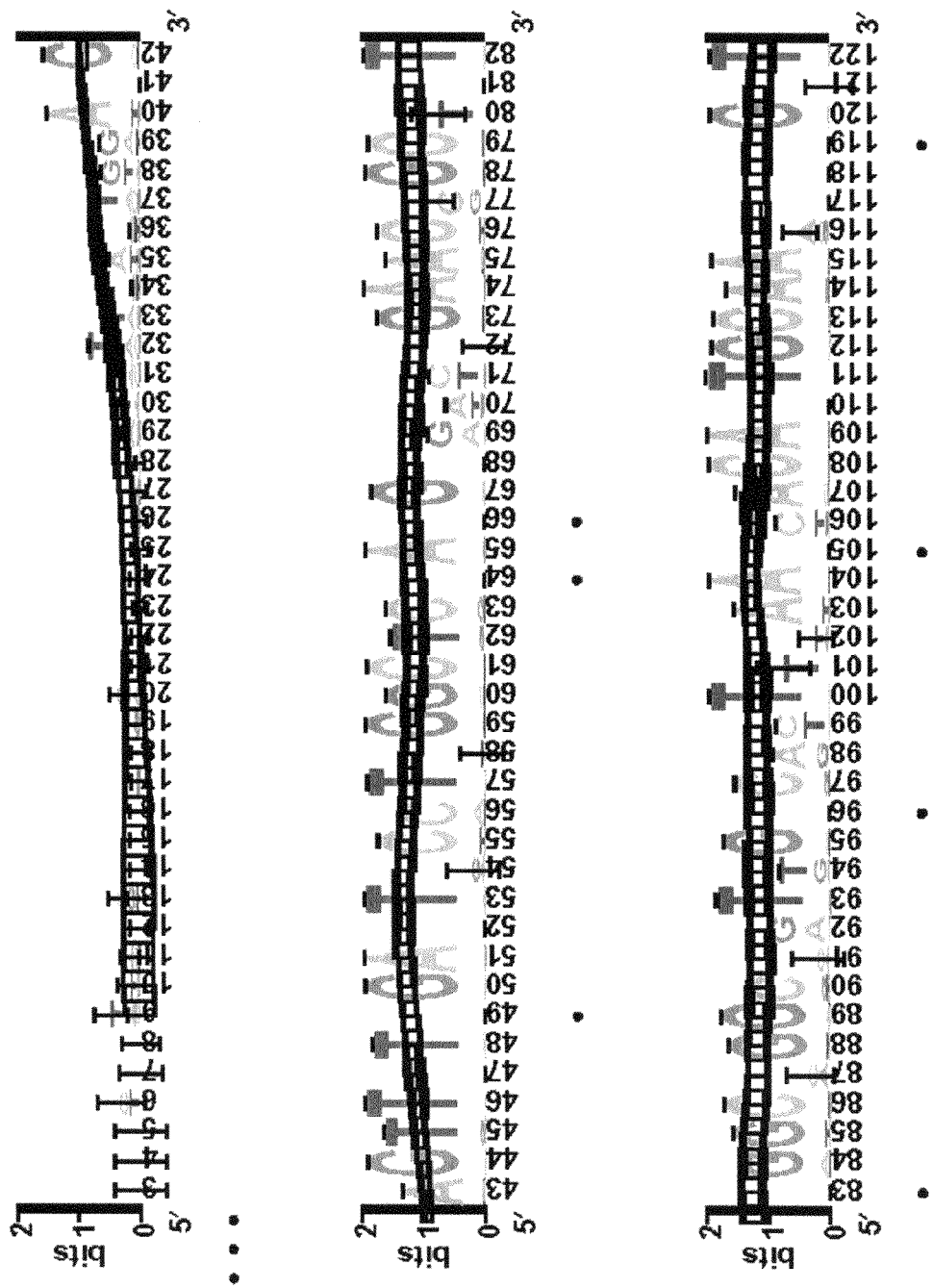
FIG. 6 is a sequence logo constructed based on a portion of the 16S rRNA genes of 3296 type strains of different bacterial species.
Figure 8:
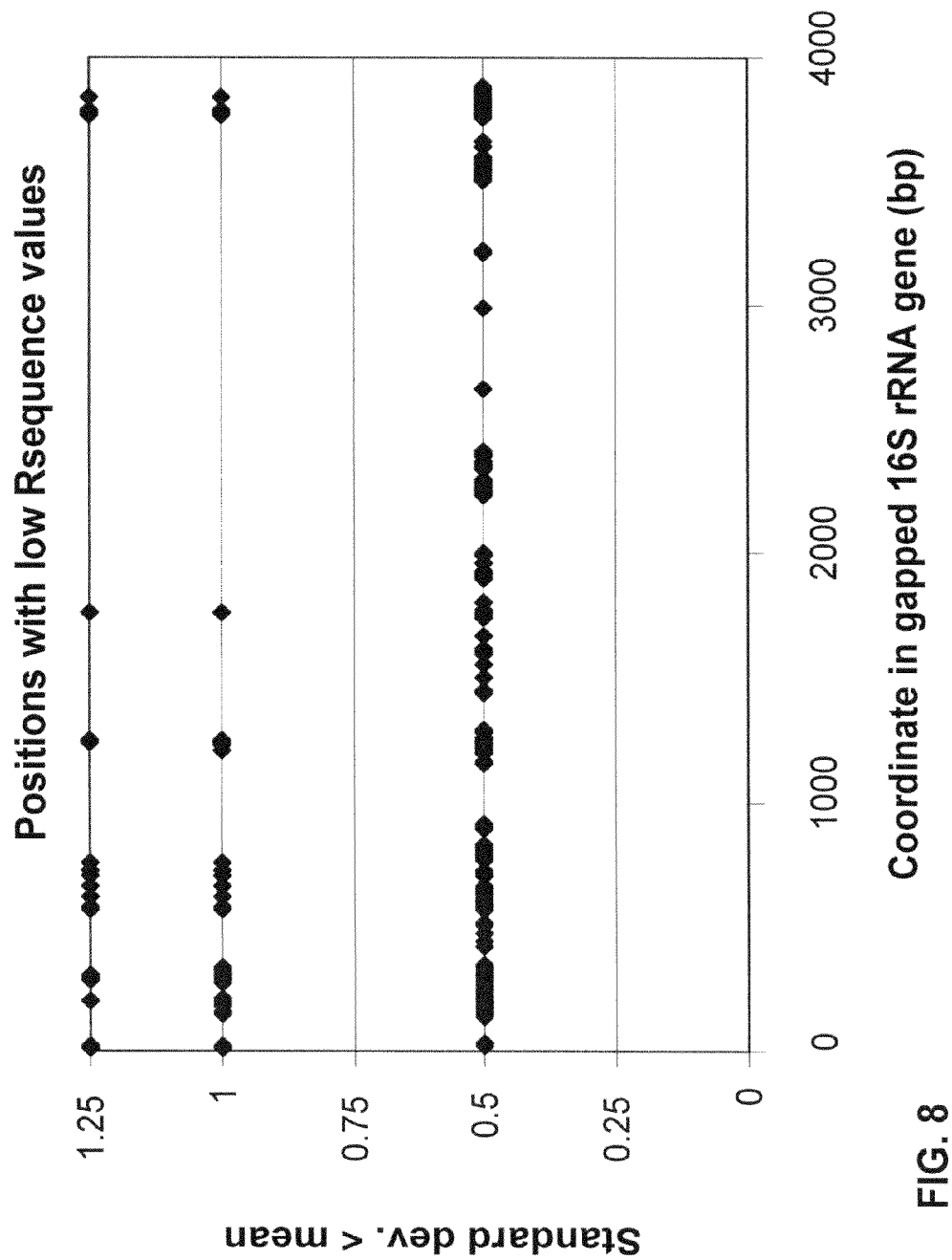
FIG. 8 shows diagrammatically nucleotide positions with low $R_{sequence}$ value.
Figure 9:
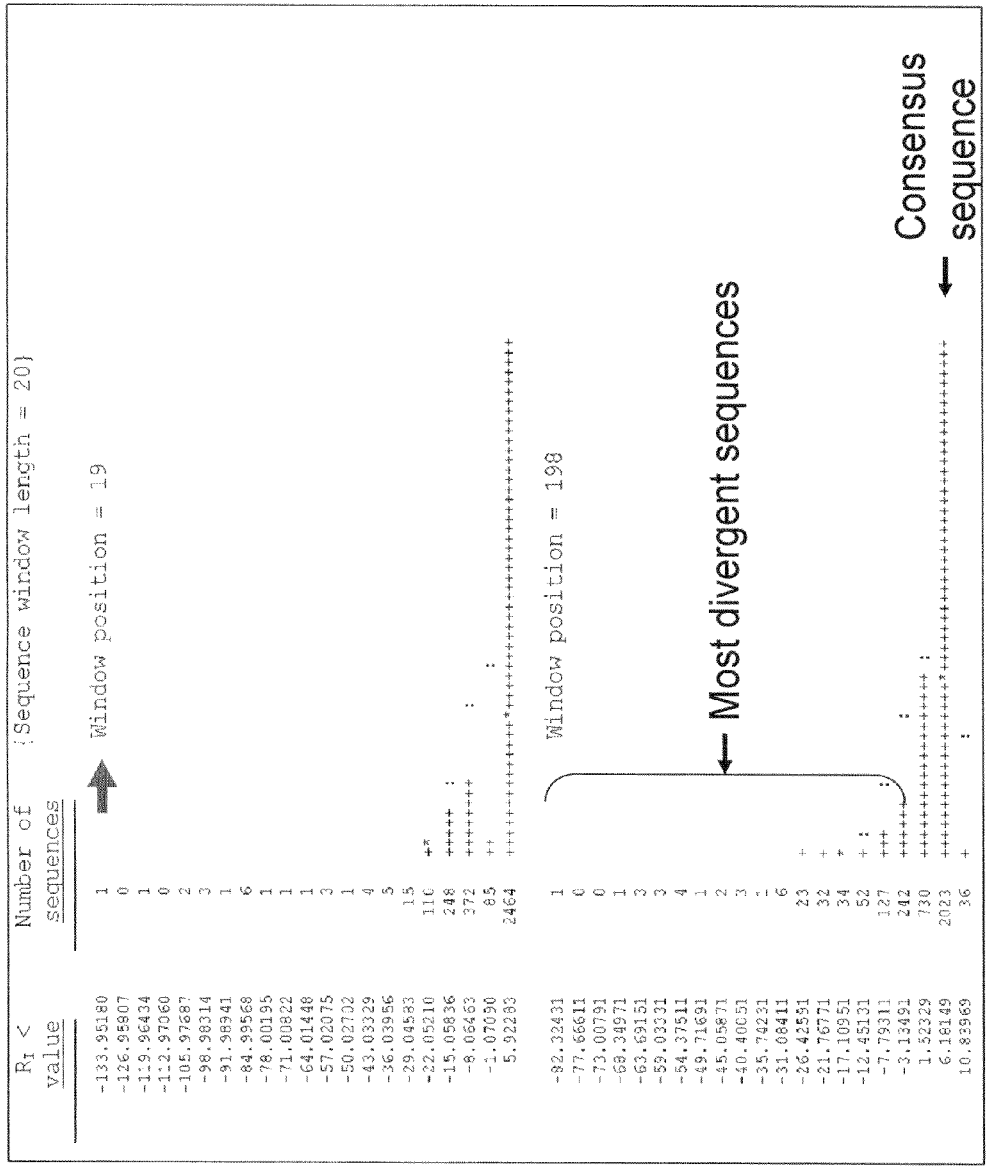
FIG. 9 shows a rank ordering of divergent "primer" sequences based on $R_i$ values.

U.S. Pat. No. 5,849,492 (the '492 patent) describes methods and primer sequences for 16S rDNA and 28S rDNA for identification of prokaryotic and eukaryotic organisms, respectively. U.S. Pat. No. 5,867,402 (the '402 patent) describes applications of information theory-based analysis of nucleic acid sequences for the purpose of analyzing binding sites in DNA or RNA that may be recognized by proteins. Individual nucleic acid sequences comprising a set of related binding sites recognized by the same protein may be rank-ordered based on their respective individual information contents. The rankings correspond to the thermodynamic stability of the interactions between the sequence and the cognate protein. The teachings of the '492 and '402 patents are hereby expressly incorporated into this disclosure by reference.

According to the present disclosure, nucleic acid rankings of related sequences that are determined from their respective individual information contents may be used to select oligonucleotides that may possess the desired properties for specific hybridization to particular sequences. The analysis of individual information content as disclosed herein does not require recognition of the sequence by a protein or potential binding agents. Rather, the presently disclosed methodology relies on the information content inherent in individual sequences being analyzed.

Briefly, information (in bits) may be used to precisely quantify both the similarities and divergence among DNA sequences, because information measures the number of choices between two equally likely possibilities (Schneider et al., *J. Mol. Biol.* 188: 415-431, 1986). The individual information, $R_i$, of a single member of a sequence family is the dot product of that sequence vector and a weight matrix, $R_i(b,l)$, based on the base frequencies at each position of the sequence according to the formula as follows:

$$R_i(j) = \sum_1^t \sum_{b=a} s(b, l, j) R_{iw}(b, l) \text{ (bits per site } j) \quad \text{I}$$

The average of the set of $R_i$ values for a family of sequences is $R_{sequence}$. The average information in bits of a related set of sequences, $R_{sequence}$, represents the total sequence conservation:

$$R_{sequence} = 2 - \left[ -\sum_{b=a}^t f(b, l) \log 2 f(b, l) + e(n(l)) \right] \quad \text{II}$$

f(b,l) is the frequency of each base b at position l,
e(n(l)) is a correction for the small sample size n at position l.

A sequence logo may be constructed based on multiply aligned sequences and the $R_{sequence}$ to locate segments with high and low information content. For instance, variable positions in a multiply aligned set of 16S rDNA sequences approach zero bits and homologous or highly conserved sequences have nearly two bits in a sequence logo (Stephens & Schneider, *Nucl. Acids Res.* 18: 6097-6100, 1990), which displays the average information content ($R_{sequence}$) and frequencies of each nucleotide at each position. Windowed average information plot may be used to locate high and low average information content. A sequence window may preferably contain 20-25 nucleotides. Individual information contents of contributing sequences in low information content windows may be ranked and sequences with the lowest individual information may be selected as specific oligonucleotides that may hybridize to or amplify DNA from one species or type strain but not DNA from another species or type strain.

Thus, the present disclosure provides a methodology wherein a set of related sequences are first aligned and scanned in search for oligonucleotides that discriminate one or more sequences from amongst the set of related sequences. This algorithm is related to another approach described by Herwig et al., in that both use Shannon information as the key criterion to select the locations in the sequences from which probes are derived. R. Herwig, et al., Information theoretical probe selection for hybridisation experiments. *Bioinformatics*, Vol. 16, 890-98 (2000). The sequence logo is a visual depiction of Shannon information (or average information content among a set of sequences). However, key differences exist between the presently disclosed approach and the one reported by Herwig. The Herwig et al. algorithm is intended to be executed using unaligned sequences with a goal to find a unique probe in a library of cDNA clones. Accordingly, the Herwig et al. algorithm identifies individual sequences with a required clustering algorithm which partitions the training set of sequences until a heuristic threshold is met.

By contrast, the method disclosed herein starts with a set of aligned related sequences from different species or type strains and does not require a partitioning step. Instead, individual information of each sequence in the aligned set, which is different from Shannon information, is computed. The difference between the information content used here and the Shannon information is illustrated in the '402 patent.

The term "related sequences" is used here to refer to polynucleotide sequences that are closely related phylogenetically. For purpose of this disclosure, related sequences may typically be aligned unambiguously with one another and the sequence identity among the aligned nucleotide sequences is at least 60%, and preferably higher than 70%. Examples of related sequences may include but are not limited to homologous, orthologous or allelic sequences that differ by at least one nucleotide. In the case of sequences from different type strains of the same species, the sequences are typically derived from the same gene (or gene family in the case of ribosomal RNA) and represent allelic variations or combinations thereof.

When a polynucleotide molecule has been identified and is known to be present in an organism, it can be said that the polynucleotide molecule is known to exist in said organism.

In one aspect, average information (or information content) is used to locate a segment or a sequence window with low overall conservation levels among the aligned sequences. The primers (or probes) that are usually species-specific or type-strain specific (in the case of PRRV) are those with low individual information in that same sequence window that is found to have low average information content. There may be more than one species-specific or type-strain specific primers (or probes) with low individual information, each detecting a different species or strain. However, within the same sequence window, there are also individual sequences which are well-conserved and have average to high levels of individual information. These sequences are generally not suitable for use as species-specific or type strain-specific oligonucleotide primers (or probes) because they are more likely to exhibit hybridization properties found in other strains or species.

After an oligonucleotide has been selected, hybridization of the selected oligonucleotide to DNA from a target organism may be performed using Southern blot or other hybridization techniques. Alternatively, the oligonucleotides may be used as primers to amplify DNA isolated from a target organism by polymerase chain reaction (PCR). The presence or absence of hybridization or amplification products indicate whether the target organism's DNA is present in the collected specimen. The Southern Blot and PCR techniques are as described by Sambrook and Maniatis, 1989, *Molecular Cloning: a Laboratory Manual,* 2nd. ed. Cold Spring Harbor Laboratory Press, NY.

The methodology for designing oligonucleotides to identify an organism through DNA hybridization or amplification may be useful in the development of automating diagnostic test and in retrieval of particular genes among families of related sequences. The target organism may be selected from a diverse range of species including but not limited to human, animal, plant, fungal, bacterial and viral origin.

In one embodiment, the methods may be applied to obtain the exact identity of porcine reproductive and respiratory syndrome virus (PRRV). Sequence logos may be constructed by aligning sequences of multiple PRRV strains. A representative segment of a logo at positions 735-814 of PRRV envelope gene is shown in FIG. 1. The box at each position indicates running average information, and the window length ranges from 20 to 25 nucleotides.

The average of the information values is the area under the sequence logo, as illustrated in FIG. 2. For purpose of primer design, $R_i$ may be below 0. A windowed information plot may be generated based on the calculated information content of each window throughout the entire segment (FIG. 3). FIG. 4 shows the distribution of $R_i$ values at position 770 of the sequence logo with a window length of 23 nucleotides. FIG. 5 shows some examples of primer sequences with high or low information content and the GenBank accession number of the sequence from which they are derived. Primers with low information content are sequence-specific and may be used to distinguish specific viral strain. Either DNA hybridization or PCR techniques may be employed for this purpose. Primers with high information content may resemble a "consensus" sequence in a multi-alignment of sequences and may be useful in selecting amplification primers for strain-independent PCR of the viral genomic DNA.

In another embodiment of the present disclosure, bacteria 16S rDNA may be used to design oligonucleotides that are specific to certain strain. Based on a large number of type strain sequences (n=3296), compute sequence logo of a given strand showing moving average may be constructed. Typical window length is between 20 and 25 nucleotides (nt). An example of a partial sequence logo is shown in FIG. 6, where the average $R_{sequence}$=0.68 bits/position. The red solid arrow indicates a position with low $R_{sequence}$. Black dots show positions with >50% gapped nucleotides. Those positions with high frequencies of gaps may be noted at this step for later use.

$R_{sequence}$ may then be calculated and a histogram of $R_{sequence}$ values for each 19-24 nucleotide (nt) window may be generated. FIG. 7 shows an example of a histogram of $R_{sequence}$/bp values for 16S rDNA windows. Coordinates with $R_{sequence}$<1.25, 1.0, 0.5 S.D. below $R_{sequence}$ of the complete 16S gene may be identified, as shown in FIG. 8. High frequency gap positions may be excluded at this step. The $R_i$ for each bacterial sequence in each low $R_{sequence}$ window may then be computed and a list of $R_i$ values for each window may be sorted to select those with the lowest $R_i$ values, as shown in FIG. 9. Gap nucleotides from sequences with lowest $R_i$ values may be removed. The resultant sequences represent the least conserved sequences at those positions with the lowest overall conservation and may be used to hybridize to or amplify a target DNA with maximum specificity.

A post-processing of low $R_i$ sequences selected according to the methodology described above may be desirable to select the best oligonucleotides. In this process, all potential primer sequences containing large gaps (>6 consecutive positions) are preferably removed. If a target species has been selected as the desired species to be identified, one may desire to select all potential "primers" for the desired species and determine their ranks for each low $R_{sequence}$ sequence window. All gap nucleotides from these potential "primers" may be removed. It is preferred that overlapping low $R_i$ sequences from the same species be combined to increase sequence length of the selected oligonucleotides. Some of the oligonucleotides selected to validate specific amplification of beer spoilage bacteria strains in silico according to the disclosed methodology are summarized in the table as shown in FIG. 10.

The following examples illustrate the present invention. These examples are provided for purposes of illustration only and are not intended to be limiting. The chemicals and other ingredients are presented as typical components or reactants, and various modification may be derived in view of the foregoing disclosure within the scope of the invention.

Example 1

Amplification of *L. brevis* DNA

Five sets of primers were tested in the lab for their ability to efficiently and selectively amplify *L. brevis* contamination in a background of S. cerevisiae DNA. The PCR primers were designed to have a broad specificity to Lactobacilli and Pediococci, while having low sequence homology to bacteria from other genera. The primers were tested for specificity using Lactobacillus brevis genomic DNA as a positive control and against S. cerevisiae and E. coli genomic DNA.

The following primers were synthesized by Integrated DNA Technologies, and were resuspended in 10 mM Tris-HCl, 1 mM EDTA, pH 8.0. Ped134F (Tm=56.6), PedLac266F (Tm=56.1), PedLac266R (Tm=56.1), PedLac266Falt (Tm=57.2), PedLac266Ralt (Tm=57.2), Lac681F (Tm=54), Lac681R (Tm=54), Lac1526R (Tm=53), Lacid1024 (Tm=54), Lacid1071R (Tm=55). The sequences of these oligonucleotides are shown below. R stands for any purine (G or A), Y stands for any pyrimidine (T/U or C), W stands for nucleotides that can only form weak interactions, namely, 2 H-bonds (A or T/U). These degenerate nucleotide positions were introduced in order to amplify multiple of these beer spoilage species in the same reaction. For example, SEQ ID NO. 33 contains three degenerate nucleotides (Y at positions 1 and 3 and R at position 4) making it capable of hybridization to both P. damnosus and P. parvulus. Nevertheless, the sequences for these two species both exhibit very low $R_i$ values (>1 S.D. below $R_{sequence}$) in this particular sequence window of all species analyzed, indicating that this sequence maximizes the divergence relative to the other sequences from other species in the alignment. Use of primers containing degenerate nucleotides that also have low $R_i$ values saves the cost of developing separate assays for each of the related species, when a single one would serve the purpose of detecting these organisms, either of which can spoil beverages or reduce ethanol yields in industrial fermentation of biomaterials to produce ethanol. For similar reasons, SEQ ID Nos 34, 35, 36, and 37 in Table 1 also contain degenerate nucleotides.

TABLE 1

Primer Sequences

| Primer name | Sequence | SEQ ID NO. |
|---|---|---|
| Ped134F | 5'-YAYRAAGTGAGTGGCGAACG-3' | 33 |
| PedLac266R | 5'-GGWYCATCCAGAAGYGATAGC-3' | 34 |
| PedLac266Ralt | 5'-GGTCCATCCAGAAGYGATAGC-3' | 35 |
| PedLac266F | 5'-GCTATCRCTTCTGGATGRWCC-3' | 36 |
| PedLac266Falt | 5'-GCTATCRCTTCTGGATGGACC-3' | 37 |
| Lac681R | 5'-CCAGTTTCCGATGCACTT-3' | 38 |
| Lac681F | 5'-AAGTGCATCGGAAACTGG-3' | 39 |
| Lac1526R | 5'-CCCTAATCATCTGTCCCAC-3' | 40 |
| Lacid1024F | 5'-GTGCAATCCGTAGAGATACG-3' | 41 |
| Lacid1071R | 5'-CCACCTGTCTTAGTGTCCC-3' | 42 |

Oligonucleotide primers aliquots of 5 μM primer pairs were prepared by mixing corresponding primers 1:1 to reduce freeze-thaw. L. brevis genomic DNA (gDNA), E. coli gDNA, S. cerevisiae genomic DNA were used as templates. Human genomic DNA was used for standard curve generation. Human β-actin control primers of 10 μM were prepared with 10 mM Tris-HCl pH 8.0. Amplification was detected quantitatively by addition of SYBR Green to reactions run on a Roche Lightcycler. Results were compared with a test kit from GEN-IAL, Ltd (Primer set #1). Unlike the assay described in this disclosure, the GEN-IAL kit, however, cannot distinguish among species from the genus of Lactobacillus. GEN-IAL's sequences are proprietary (which may include multiple sets of primers) and are not provided with their kit.

Figure 11:
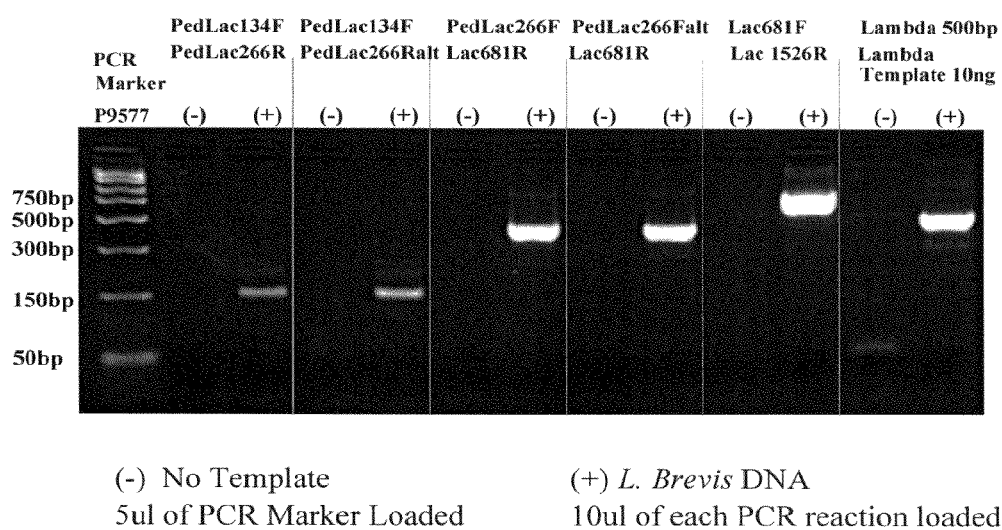
FIG. 11 shows results of initial PCR tests with the following primer pairs using L. brevis gDNA: Ped134F/PedLac266R, Ped134F/PedLac266Ralt, PedLac266F/Lac681R, PedLac266Falt/Lac681R, and Lac681F/Lac1526R.

Initial tests were conducted simply by performing standard PCR using JumpStart Red Taq (Sigma). The following primer pairs were tested using L. brevis gDNA at a final concentration of 250 pM: Ped134F/PedLac266R, Ped134F/PedLac266Ralt, PedLac266F/Lac681R, PedLac266Falt/Lac681R, and Lac681F/Lac1526R. The results are shown in FIG. 11.

The yield for the amplicons generated by PedLac134F were slightly less than that of the other amplicons. This was expected since PedLac134F had a lessened affinity for L. brevis and would only amplify at conditions of low stringency. All other primer pairs yielded a specific product matching the expected size. Negative controls without template showed no observable amplification.

To examine the primer sets on a quantitative PCR based system, we initially tested them with the Lightcycler Fast Start DNA Master SYBR Green Kit (Roche). It should be noted that the primer annealing temperature for this experiment was 52° C. Amplification is detected by the increase in fluorescence produced when SYBR Green I intercalates with dsDNA product.

Figure 12:
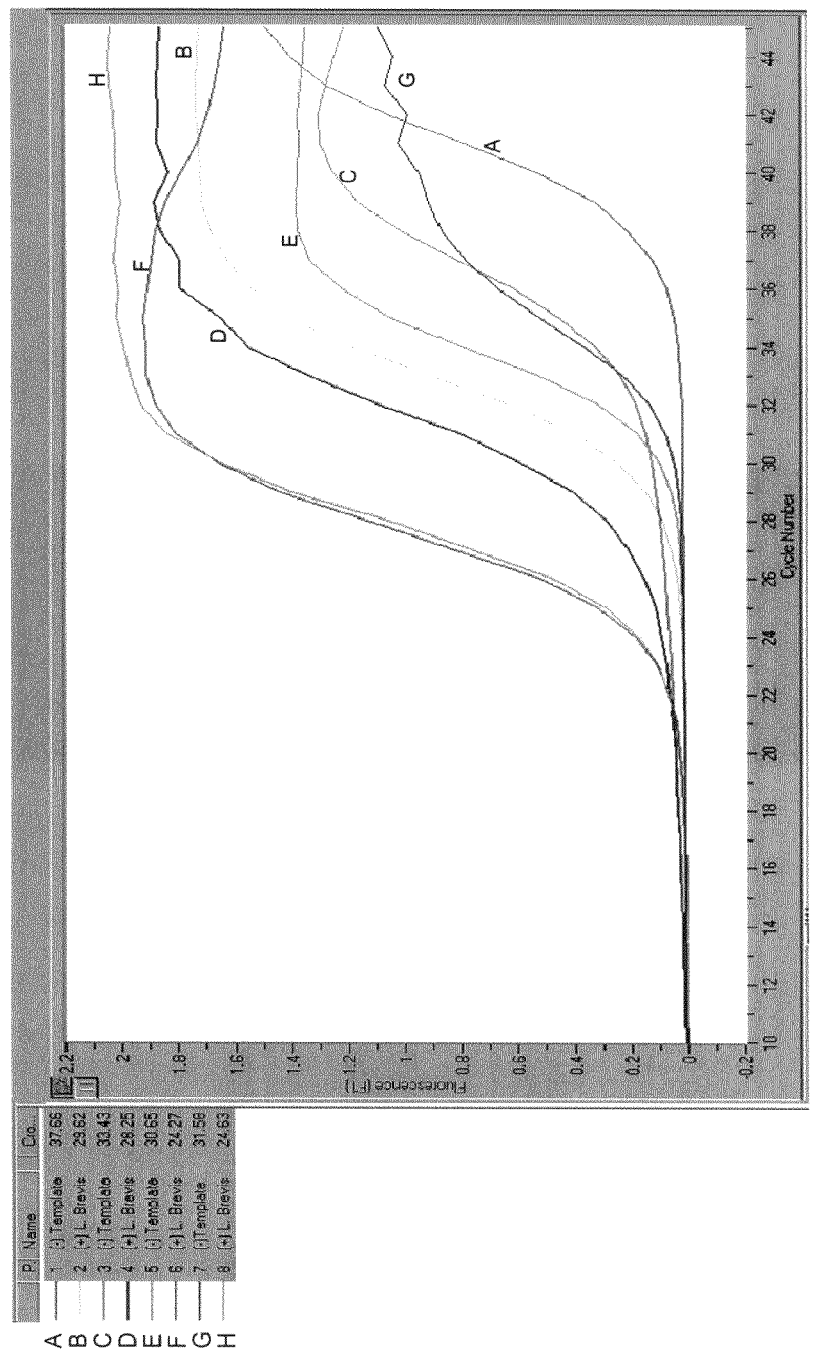
FIG. 12 is a quantitative PCR (qPCR) plot comparing the primers of the present disclosure against the GEN-IAL primer mix #1 with and without the addition of L. brevis DNA.

The quantitative PCR (qPCR) plot in FIG. 12 compares the primers of the present disclosure vs. the GEN-IAL primer mix #1 with and without the addition of L. brevis DNA. The cycle number at which a statistically relevant increase in fluorescence occurs is the cycle threshold ($C_T$). Therefore, PCR efficiency is inversely proportional to the $C_T$ number. Amplification with Lac681F/Lac1526R (sample #6, blue-grey) yielded the lowest $C_T$ at 24.27, which was comparable to the 24.63 $C_T$ of the GEN-IAL Primer #1 mix (sample #8, grey). Both of these sets have the best efficiency under the conditions used. Amplification with PedLac266F/Lac681R yielded a higher $C_T$ of 28.25. The negative control (−) template reactions all showed some degree of amplification at longer cycle times, which is likely due to formation of primer-dimer products.

Figure 13:
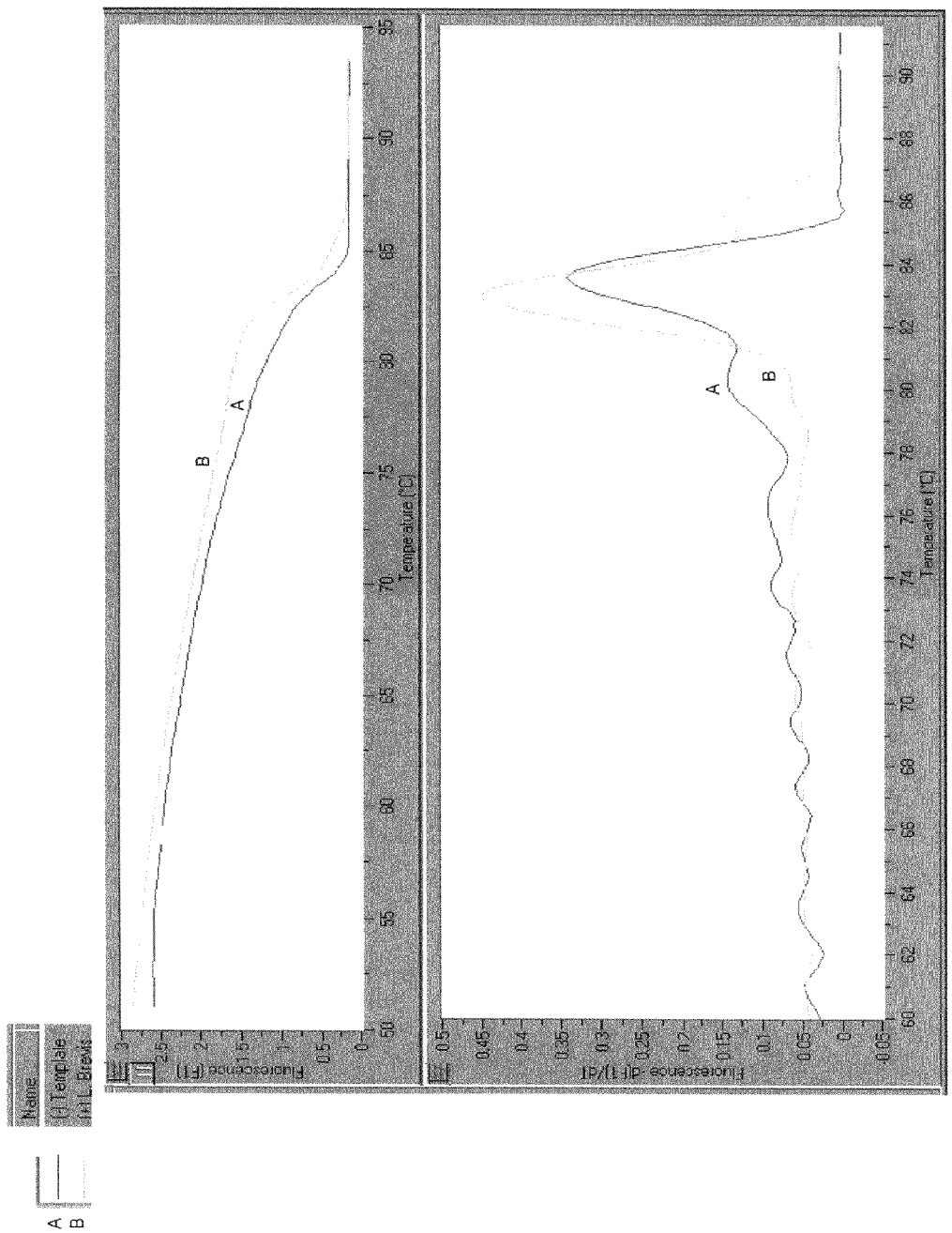
FIG. 13 shows a melt curve analysis of the Ped134F/PedLac266R sample from the amplification plot shown in FIG. 12.

The existence of small, alternate PCR products was confirmed using the melt-curve analysis software on the Light-Cycler. Using this feature, the Lightcycler monitored the fluorescence of the final PCR products with increasing temperature. As the temperature increased the fluorescence decreased due to the release of SYBR Green I molecules from the melting dsDNA products. The analysis allowed the identification of intended and unwanted by-products (primer dimers) based upon Tm calculation. FIG. 13 shows the melt curve analysis of the Ped134F/PedLac266R sample from the amplification plot shown in FIG. 12, which illustrates the specificity of the reaction. The top plot shows Fluorescence vs. time. The bottom plot is the first negative derivative (−dF/dT) vs. temperature and shows the melting peaks of the PCR products. The area under the peaks also provides information on the amount of a specific product present.

The (−) template reaction (blue) in this case yielded product with a Tm of 83.5° C. The reaction with L. brevis template present (green) yielded products having a Tm of 82.94° C. and a second less abundant product having a Tm of 85.72° C. The (+) L. brevis sample with the Ped134F/PedLac266R primer set did not yield a product that could be readily distinguishable from the blank reaction in terms of Tm and yield.

Figure 14:
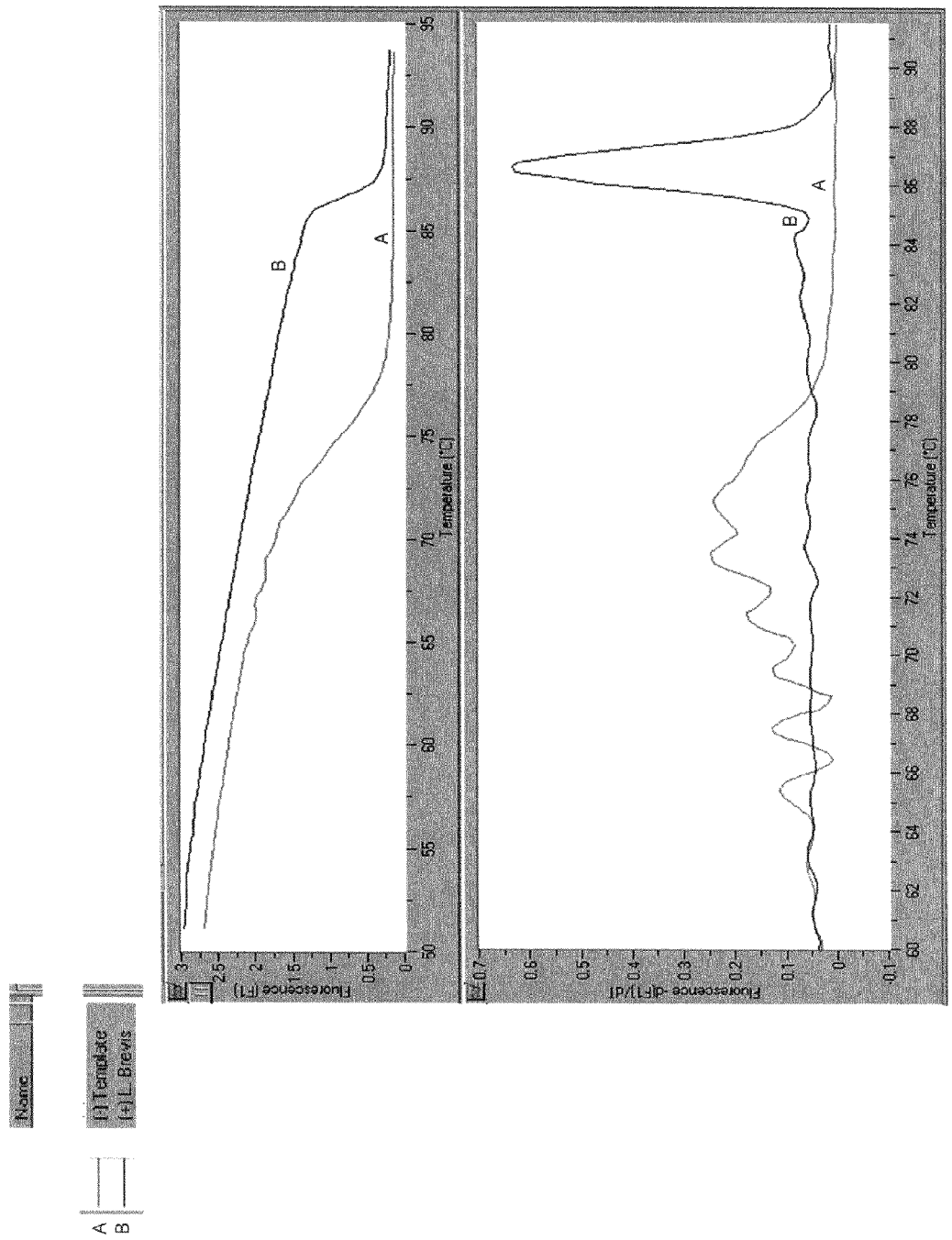
FIG. 14 shows a melt-curve analysis of the PedLac266F/Lac681R amplification.

The melt-curve analysis of the PedLac266F/Lac681R amplification is shown in FIG. 14. The (−) template reaction (red) yielded what one would expect of a reaction having a small amount of primer-dimer formation. The reaction with L. brevis template (black) yielded a specific product having a Tm of 86.63° C., easily distinguishable from the non-specific product in yield and Tm.

Figure 15:
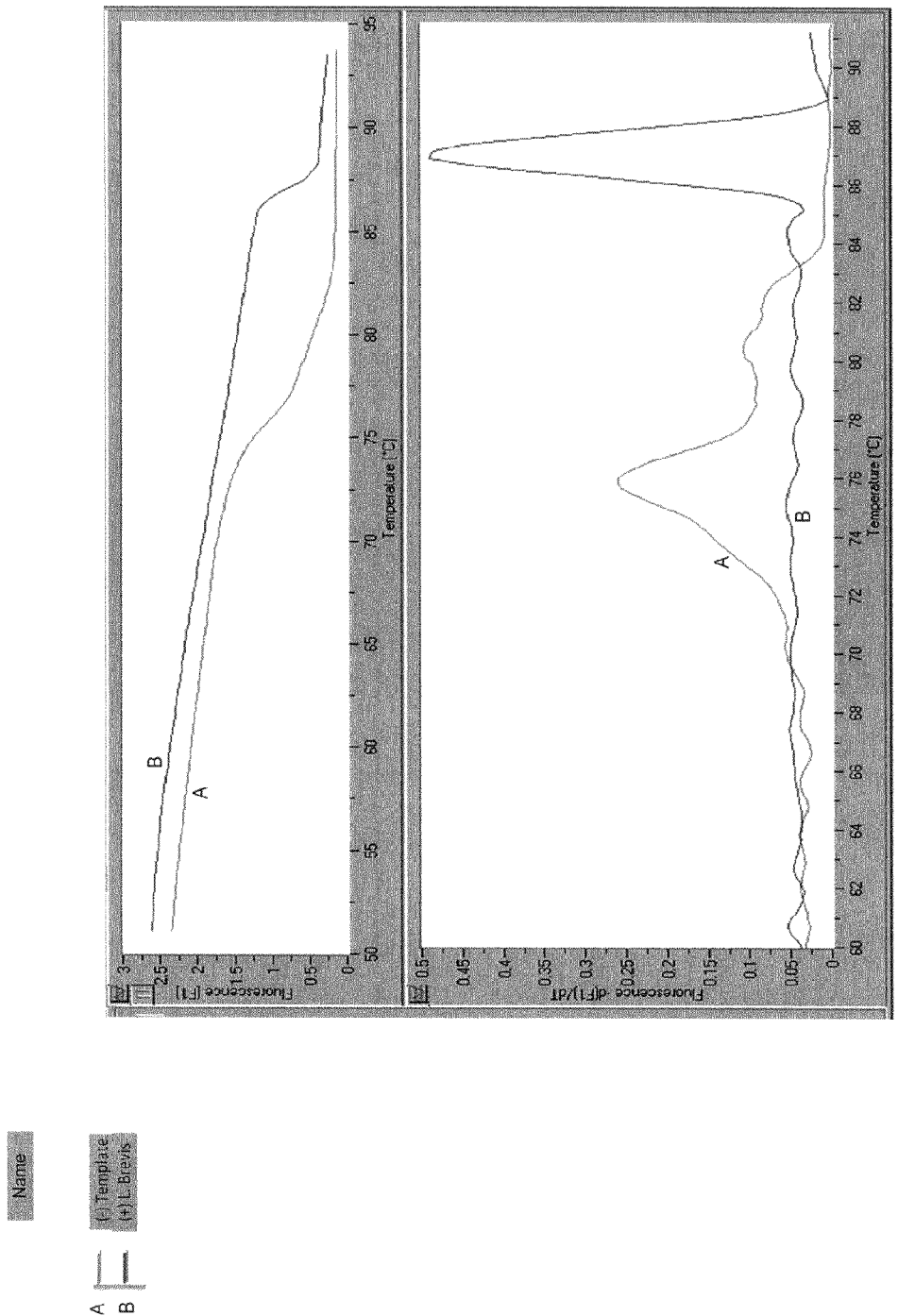
FIG. 15 shows the melting-curve analysis of the PCR using Lac681F/Lac1526R primers.

The melting-curve analysis of the Lac681F/Lac1526R reaction is shown in FIG. 15. The (−) template reaction (pink) yielded an amplicon with a broad melting profile and a Tm of approximately 75.67° C. The reaction with L. brevis template (blue-grey) yielded a specific amplicon having a Tm of 87.03° C.

Figure 16:
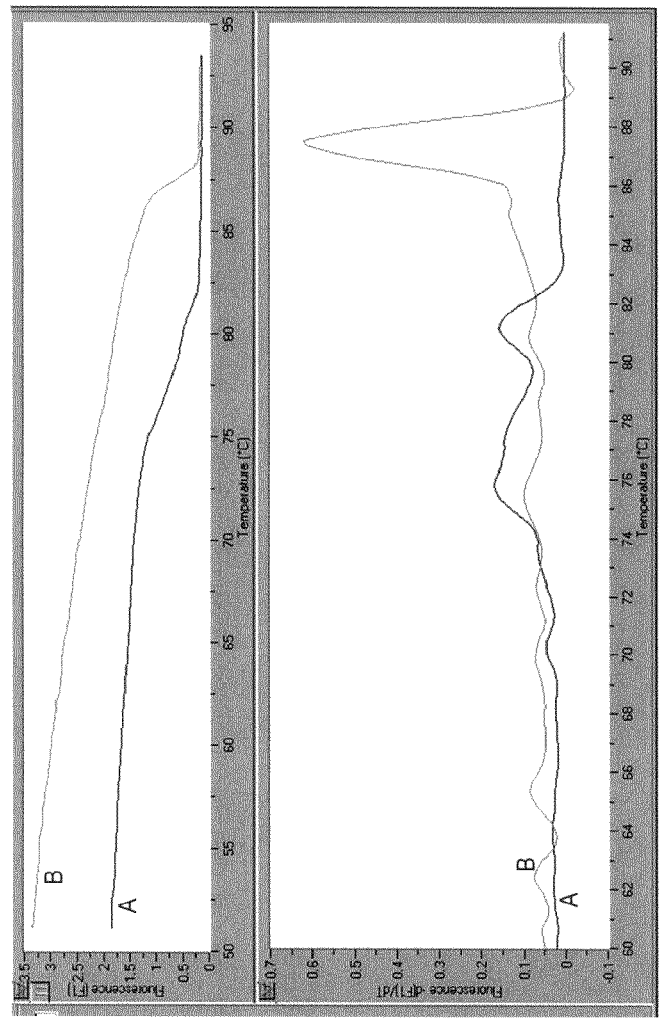
FIG. 16 shows the melt-curve analysis of the PCR using GEN-IAL Primer Mix #1.

The melt-curve analysis of the GEN-IAL Primer Mix #1 is shown in FIG. 16. The (−) template reaction (dark blue) yielded a small amount of non-specific product. The reaction containing L. brevis DNA (grey) yielded a specific amplicon having a Tm of 87.43° C. Of the primers tested, the Lac681F/Lac1526R performed the best in terms of specificity and yield when amplifying L. brevis gDNA.

Figure 17:
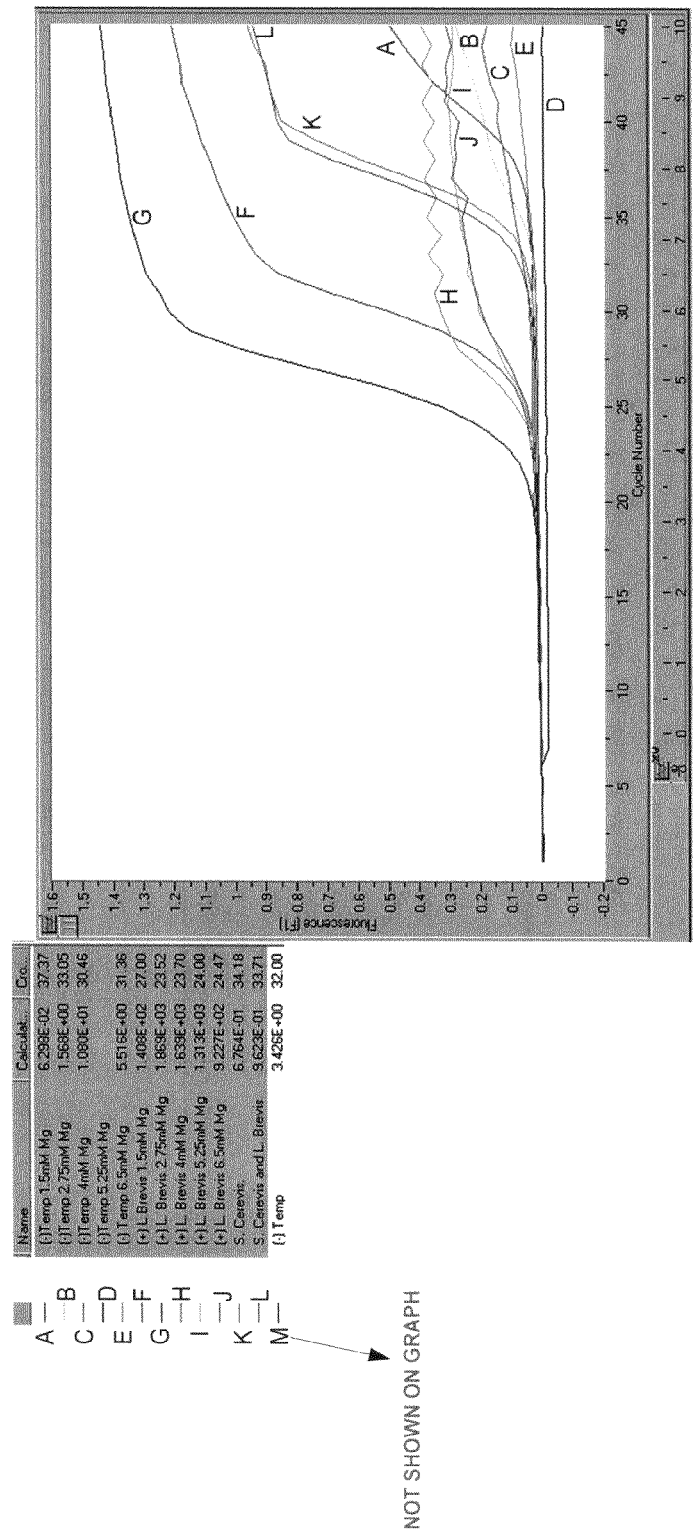
FIG. 17 shows an amplification plot of the PCR using Lac681F/Lac1526R and in the presence of *Saccharomyces cerevisiae* genomic DNA and increasing concentration of $Mg^{2+}$.

To test the specificity and yield of the primers, the Lac681F/Lac1526R primer set was tested again for L. brevis amplification. The optimized conditions for primer annealing and polymerase activity were partly determined by titrating magnesium ion in the reactions. Negative controls without the addition of L. brevis template were performed for each concentration of $Mg^{2+}$. The specificity of the primers was also tested against the introduction of Saccharomyces cerevisiae genomic DNA. The amplification plot is shown in FIG. 17. The 2.75 mM $Mg^{2+}$ reaction (#7, dark blue) had the lowest $C_T$ with a value of 23.52, as well as the highest yield of final product. The reaction containing S. cerevisiae gDNA (0.2 ng/ul, #11, yellow) had a $C_T$ of 34.18 which is slightly higher than the (−) template reaction (#2, green) $C_T$ of 33.05.

Figure 18:
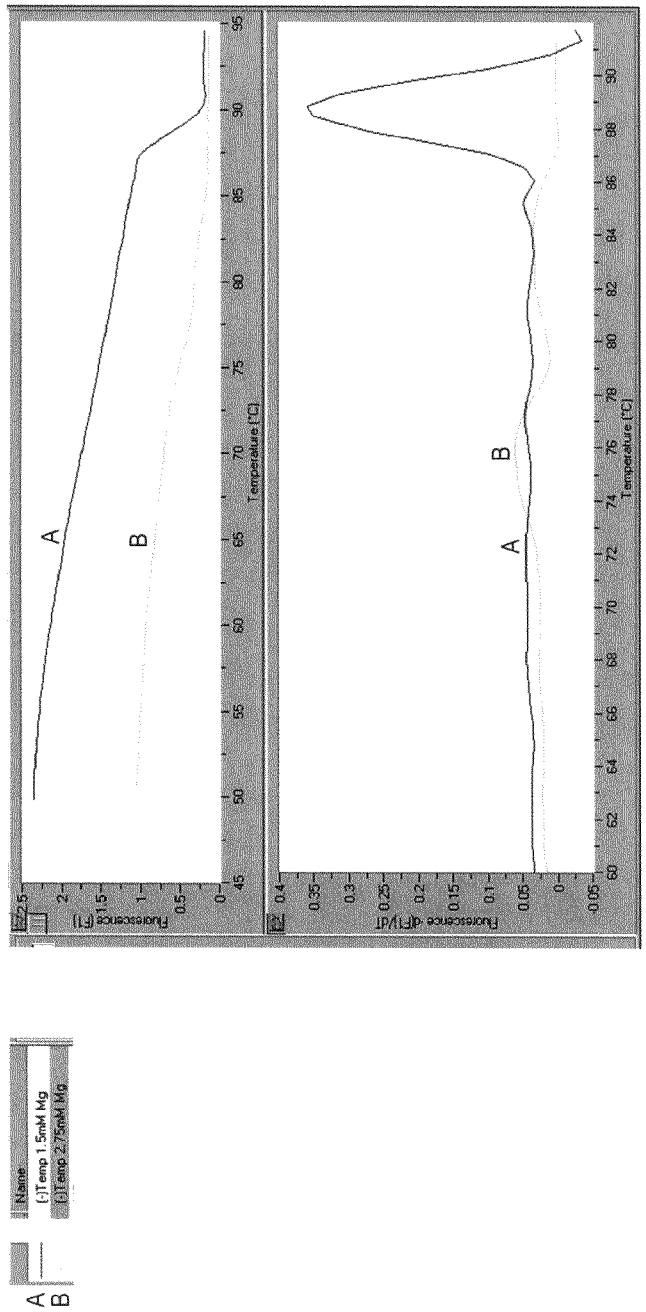
FIG. 18 shows the melting-curve analysis of the Lac681F/Lac1526R reaction with *L. brevis* gDNA.

The melting-curve analysis of the Lac681F/Lac1526R reaction with L. brevis gDNA is shown in FIG. 18. The optimal $Mg^{2+}$ concentration for the amount of primer/template/annealing-temperature used was 2.75 mM. The (+) L. brevis reaction (#7, dark blue) yielded a specific amplicon having a Tm=88.69° C. The negative control (#2, green) did not yield a significant amount of product.

Figure 19:
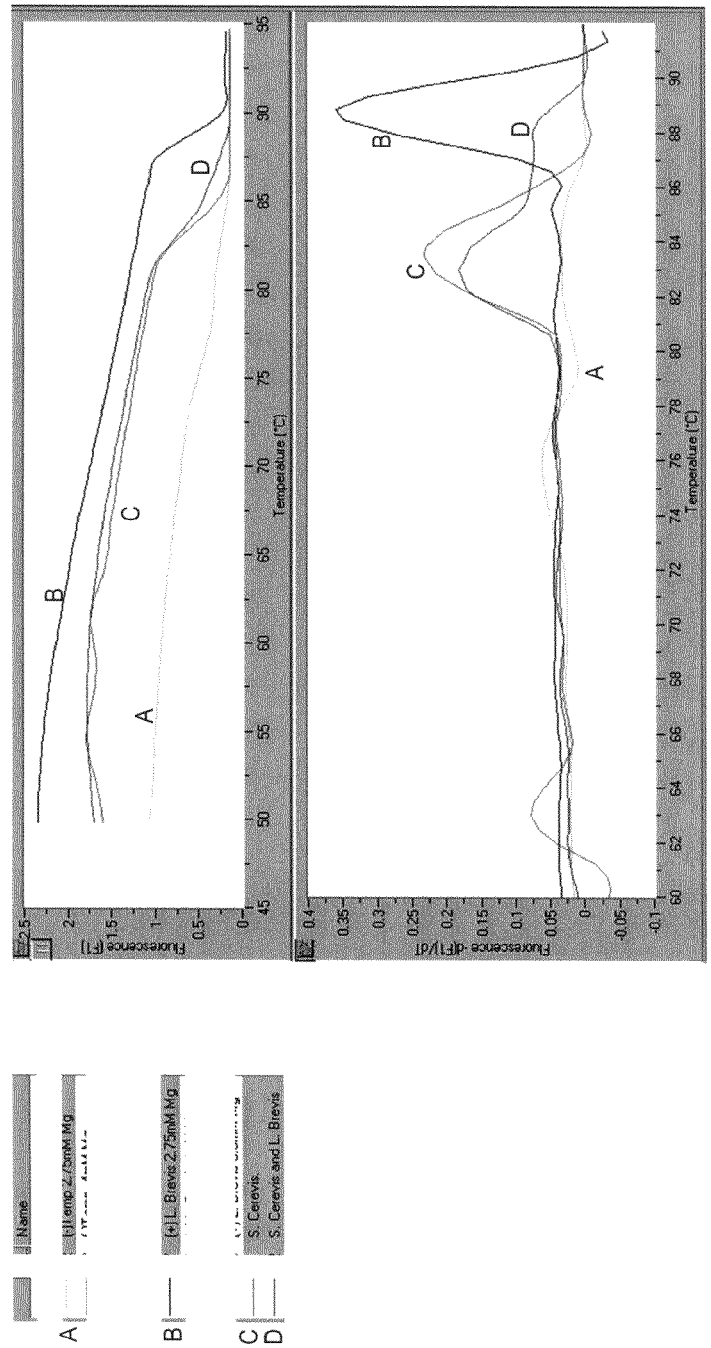
FIG. 19 shows the melting-curve analysis of the Lac681F/Lac1526R amplification reaction with *L. brevis* and *S. cerevisiae* DNA.

The melting-curve analysis of the Lac681F/Lac1526R amplification reaction with L. brevis and S. cerevisiae DNA is shown in FIG. 19. The melt-curve above shows a comparison of the L. brevis (#7,dark blue) and S. cerevisiae (#11, yellow) amplification products. The S. cerevisiae amplification yielded a defined product having a Tm=83.49° C. The amount of S. cerevisiae gDNA used was 4 ng/20 ul rxn, which was significantly high quantitative PCR. The reaction containing both 4 ng of S. cerevisiae gDNA and 1.5 ng of L. brevis gDNA (#12, blue-grey) illustrates the competition for primer annealing between the two DNA templates by the two melt peaks present.

Figure 20:
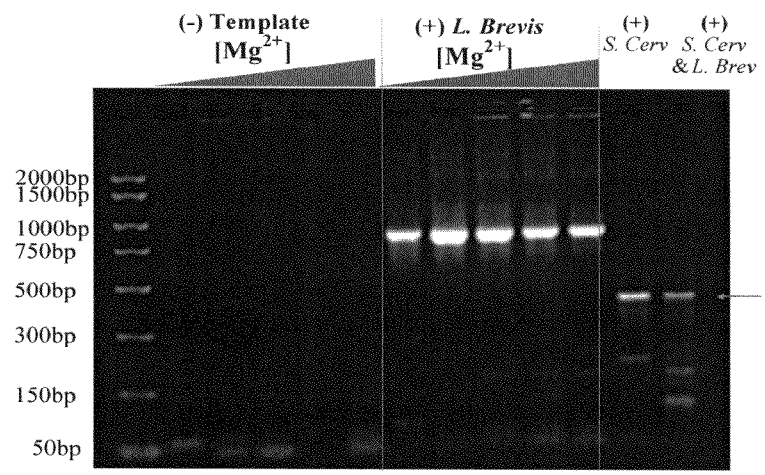
FIG. 20 shows the final amplification products of the PCR with Lac681F/Lac1526R as shown in FIG. 17 on a 2% Agarose gel.

The photograph of the gel in FIG. 20 shows the final amplification products for this experiment. The PCR reactions were allowed to proceed forty five cycles and the Lightcycler did not have a cool down function below room temperature following analysis. Therefore, some primer-dimer formation and non-specific amplification might have been enhanced on the picture. However, there is a defined amplicon for the samples containing S. cerevisiae gDNA. The low molecular weight S. cerevisiae amplicon was not significantly competed away by the addition of L. brevis gDNA, as was seen in the melt-curve analysis.

Figure 21:
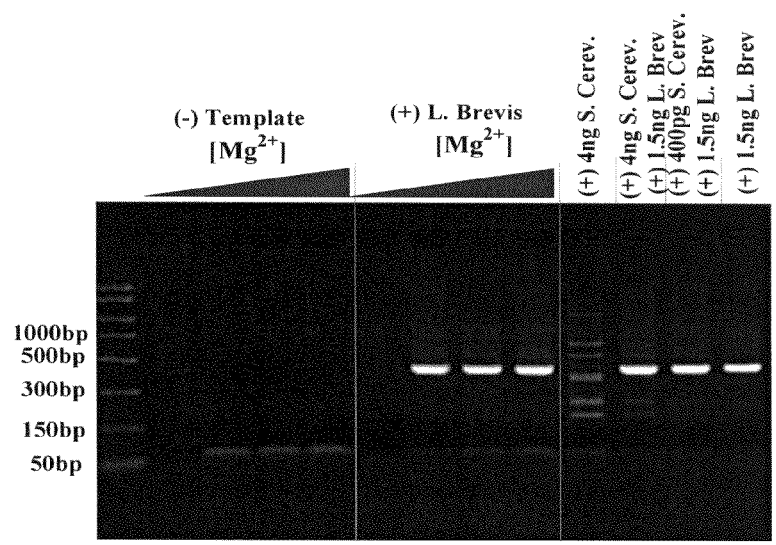
FIG. 21 shows the final amplification products of the PCR with PedLac266F/Lac681R primers on a 2% Agarose gel.

The other primer set that performed well on the initial trials was PedLac266F/Lac681R. This primer set was also tested on the Lightcycler instrument with the same experimental format as the previous primer set (annealing temperature of 50° C.). A magnesium ion titration was performed yielding the same ideal concentration as the previous primer set (2.75 mM $Mg^{2+}$, amplification plot not shown). A 2% gel of the final end-products shows that some non-specific amplification does occur with S. cerevisiae gDNA (FIG. 21). The S. cerevisiae 4 ng/20 ul reaction yielded several amplicons ranging between 150 and 1500 bps. However, the non-specific amplification is more readily competed away with the addition of L. brevis gDNA than the Lac681F/Lac1526R primer set.

Figure 22:
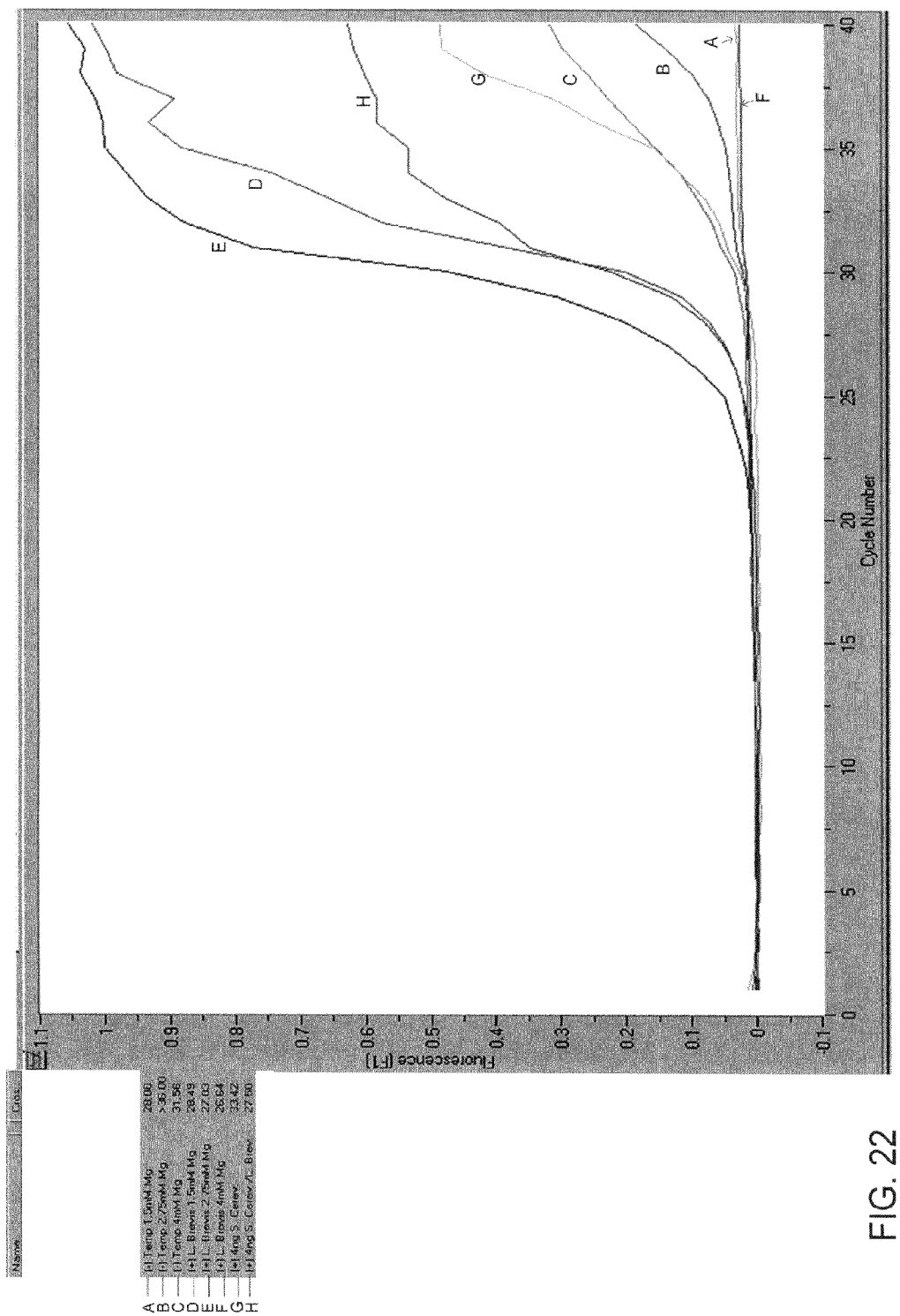
FIG. 22 shows the amplification plot of the PCR using PL266F/L681R primer set and elevated annealing temperature.

To test whether the specificity of the PedLac266F/Lac681R (PL266F/L681R) primer set could be improved, the annealing temperature for the PCR reaction was increased to 52° C. The amplification plot is shown in FIG. 22. The increased annealing temperature lessened the non-specific S. cerevisiae amplification from a 29.70$C_T$ (data not shown) to 33.42$C_T$ (#15, pink).

Figure 23:
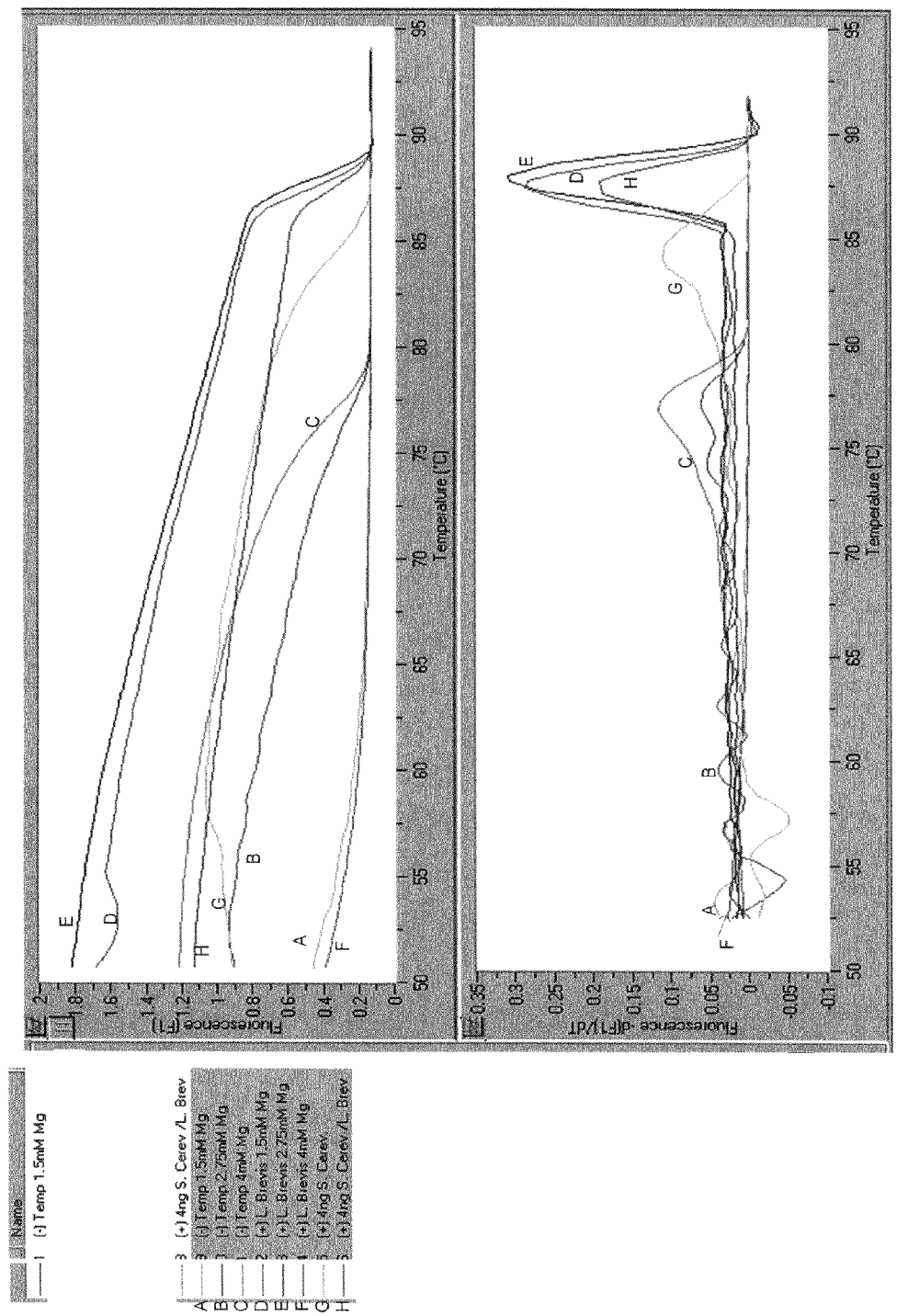
FIG. 23 shows the melt-curve analysis of the PCR using PedLac266F/Lac681R primer.

The melt-curve for the PedLac266F/Lac681R primer set is shown in FIG. 23.

Figure 24:
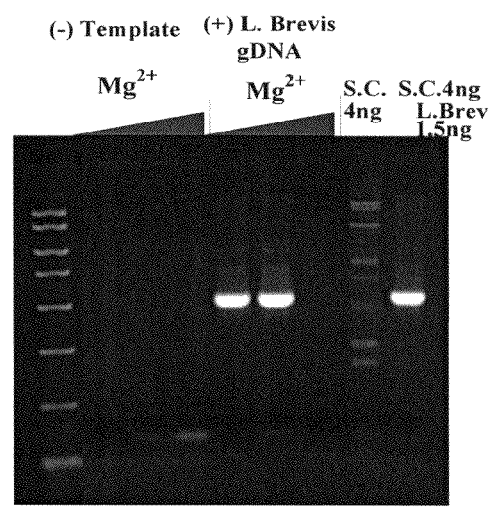
FIG. 24 shows amplification end-products of the PCR as shown in FIG. 22 on a 2% Agarose gel.

FIG. 24 shows a 2% Agarose gel of amplification end-products. The end-product gel of the PL266F/L681R amplification shows the expected product with the addition of L. brevis gDNA. The reaction with only S. cerevisiae gDNA showed distinct non-specific amplicons, however with the addition of 1.5 ng of L. brevis gDNA, the non-specific targets were out-competed by the correct template.

Figure 25:
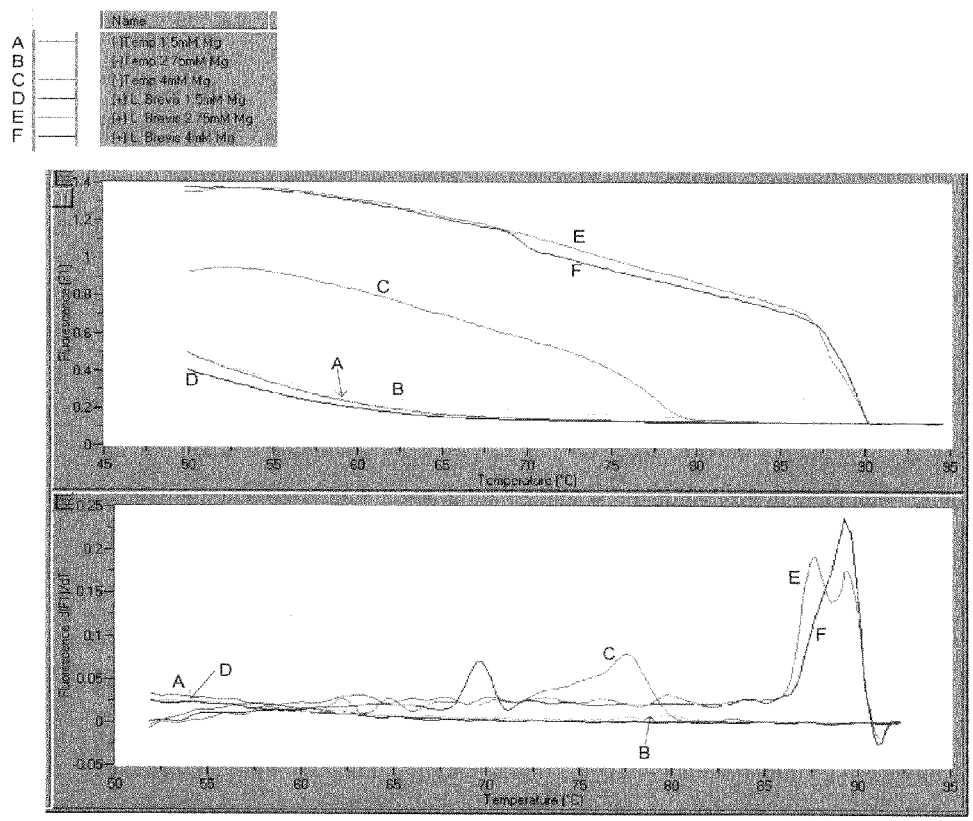
FIG. 25 shows the melt-curve analysis of the PCR using PedLac266Falt/Lac681R primer.

A similar format of experimentation was performed using the PedLac266Falt/Lac681R primer set. The PedLac266Falt oligonucleotide has a slightly higher $T_m$ (57.2° C.) than that of PedLac266F (56.1° C.). The amplification plot with the PedLac266Falt/Lac681R primer set showed a lower $C_T$ with 4 mM $Mg^{2+}$ (24.70) than with 2.75 mM $Mg^{2+}$ (27.02) (data not shown). However this can be partly attributed to added primer-dimer formation in the former as illustrated by the small melt peak at approximately 68° C. in the melt plot in FIG. 25 (#6, blue-grey). Unfortunately at 2.75 mM $Mg^{2+}$ the melt peak for the (+) L. brevis gDNA yields two detectable amplicons (#5, pink) instead of one.

Figure 26:
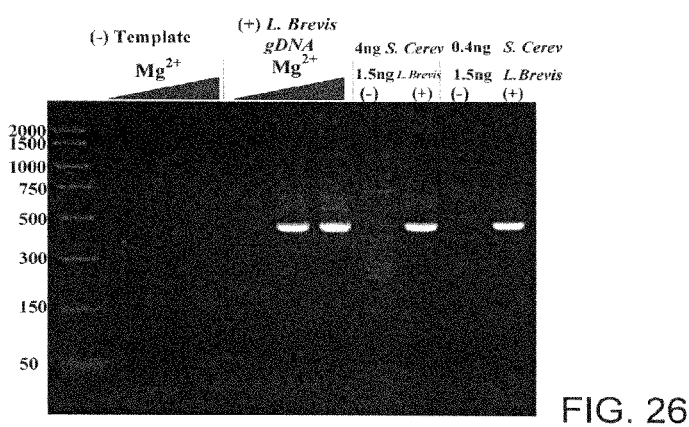
FIG. 26 shows a 2% Agarose gel of end-product amplification using the PedLac266Falt/Lac681R primer set.

FIG. 26 shows a 2% Agarose gel of end-product amplification using the PedLac266Falt/Lac681R primer set. As seen above, the non-specific products present with the addition S. cerevisiae gDNA were significantly competed away with the addition of L. brevis gDNA. The PedLac266Falt/Lac681R & PedLac266F/Lac681R primer sets were tested at slightly higher annealing temperatures of 54 and 53° C. to see if the non-specific amplification of S. cerevisiae could be eliminated. However, no amplification was detected (data not shown). This isn't surprising considering the given that the $T_m$ for Lac681R is 54° C.

Additional specificity experiments of the primer sets PedLac266Falt/Lac681R and PedLac266F/Lac681R were performed. Quantitative PCR was used to test primer affinity against E. coli Strain B gDNA. The results of the experiments showed that both the PedLac266Falt/Lac681R and PedLac266F/Lac681R primer sets yield no amplification products when presented with E. coli Strain B gDNA alone and show virtually no affinity for the template when in the presence of L. brevis gDNA (data not shown).

In conclusion, of the tested primer sets all supported amplification of the test template L. brevis gDNA and produced the expected size of amplicons. The melt profiles of the reactions were also ideal for discrimination of L. brevis amplicons. Primer specificity was tested against introduction of S. cerevisiae and E. coli gDNA. Of the primer sets tested (PedLac266F/Lac681R, PedLac266Falt/Lac681R, Lac681F/Lac1526R), all showed a low level of non-specific of amplification when challenged with S. cerevisiae gDNA and no amplification with E. coli gDNA. The PedLac266F/Lac681R and PedLac266Falt/Lac681R primer sets were shown to have significantly less affinity than Lac681F/Lac1526R for *S. cerevisiae*.

The results of the experiments described above are summarized in the following table.

TABLE 2

Amplification of *L. brevis* DNA

| Primer Set | Gel$_{(L. brevis)}$ | $C_T$ | Melt | Yeast | E. coli |
|---|---|---|---|---|---|
| PedLac 266Falt/Lac681R | Strong | 24.7 | OK | Weak | None |
| PedLac266F/Lac681R | Strong | 27.03 | Good | Weak | None |
| Lac681F/Lac1526R | Strong | 23.52 | Good | Weak | None |
| PedLac134F/PedLac 266R | Weak | X | Odd | X | X |

Example 2

Amplification of *P. damnosus* DNA

The experiments detailed in this report focused on the performance of the Ped134F/PedLac266R primer set when amplifying *P. damnosus* gDNA. The specificity of the primer set was also tested by introducing gDNA from several different organisms including, *Escherichia. coli* (ATCC #11775), *Pseudomonas fluorescens*(ATCC #13525), *Bacillus subtilis* (ATCC#6051), *Streptococcus mutans* (ATCC#35668), and *Staphylococcus epidermis* (ATCC#14990).

Oligonucleotide primers were synthesized by Integrated DNA Technologies, at a concentration of 10 μM each in 10 mM Tris-HCl, 1 mM EDTA, pH 8.0. The following primers were received: Ped134F (Tm=56.6), PedLac266F (Tm=56.1), PedLac266R (Tm=56.1), PedLac266Falt (Tm=57.2), PedLac266Ralt (Tm=57.2), Lac681F (Tm=54), Lac681R (Tm=54), Lac1526R (Tm=53), Lacid1024 (Tm=54), Lacid1071R (Tm=55). Aliquots of 5 μM primer pairs were prepared by mixing corresponding primers 1:1 to reduce freeze-thaw. Genomic DNA was prepared using the GenElute Bacterial Genomic DNA Kit (NA2100). Human genomic DNA for standard curve generation was purchased from Roche. Human β-actin were used as control primers (Sigma-Genosys). Working aliquots of 10 μM were prepared with 10 mM Tris-HCl pH 8.0. Products were detected with SYBR Green (Molecular Probes) and quantitative amplification was performed with a Lightcycler (Roche).

Figure 27:
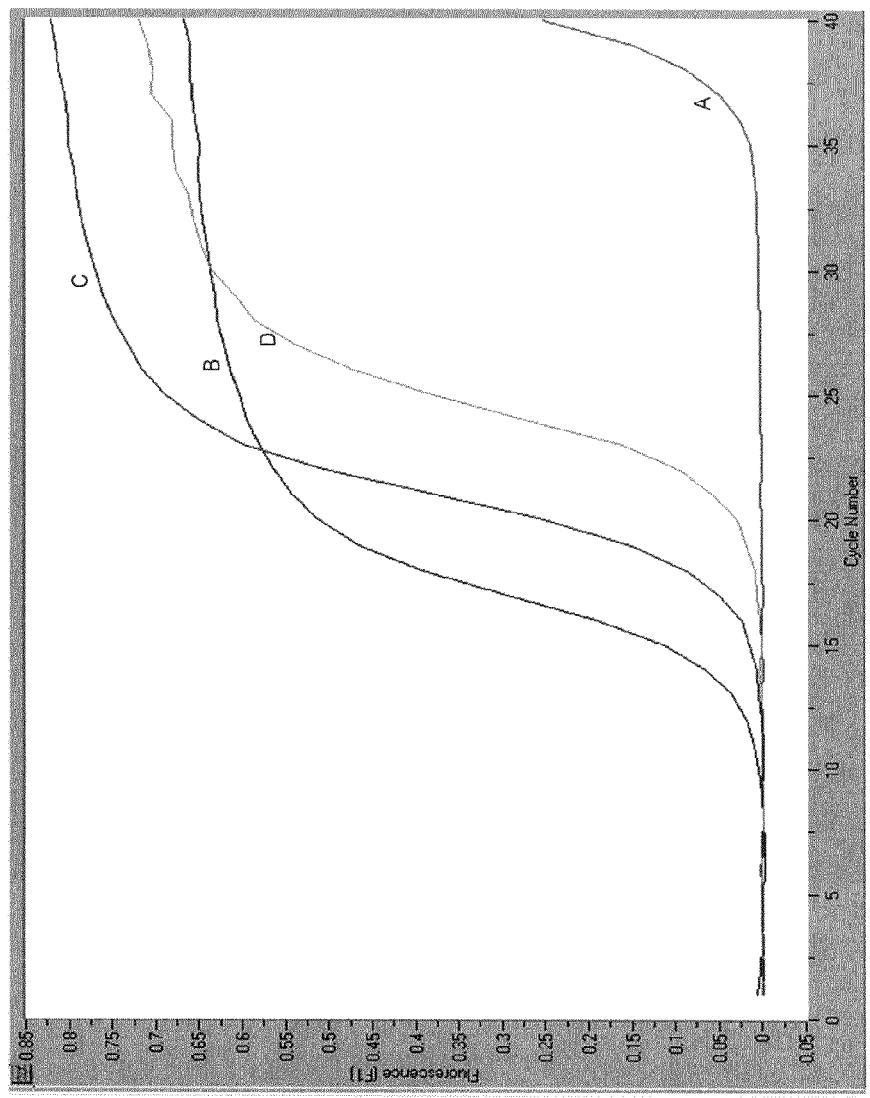
FIG. 27 shows the amplification of varying amount of *P. damnosus* gDNA using Ped134F/PedLac266R primer.
Figure 28:
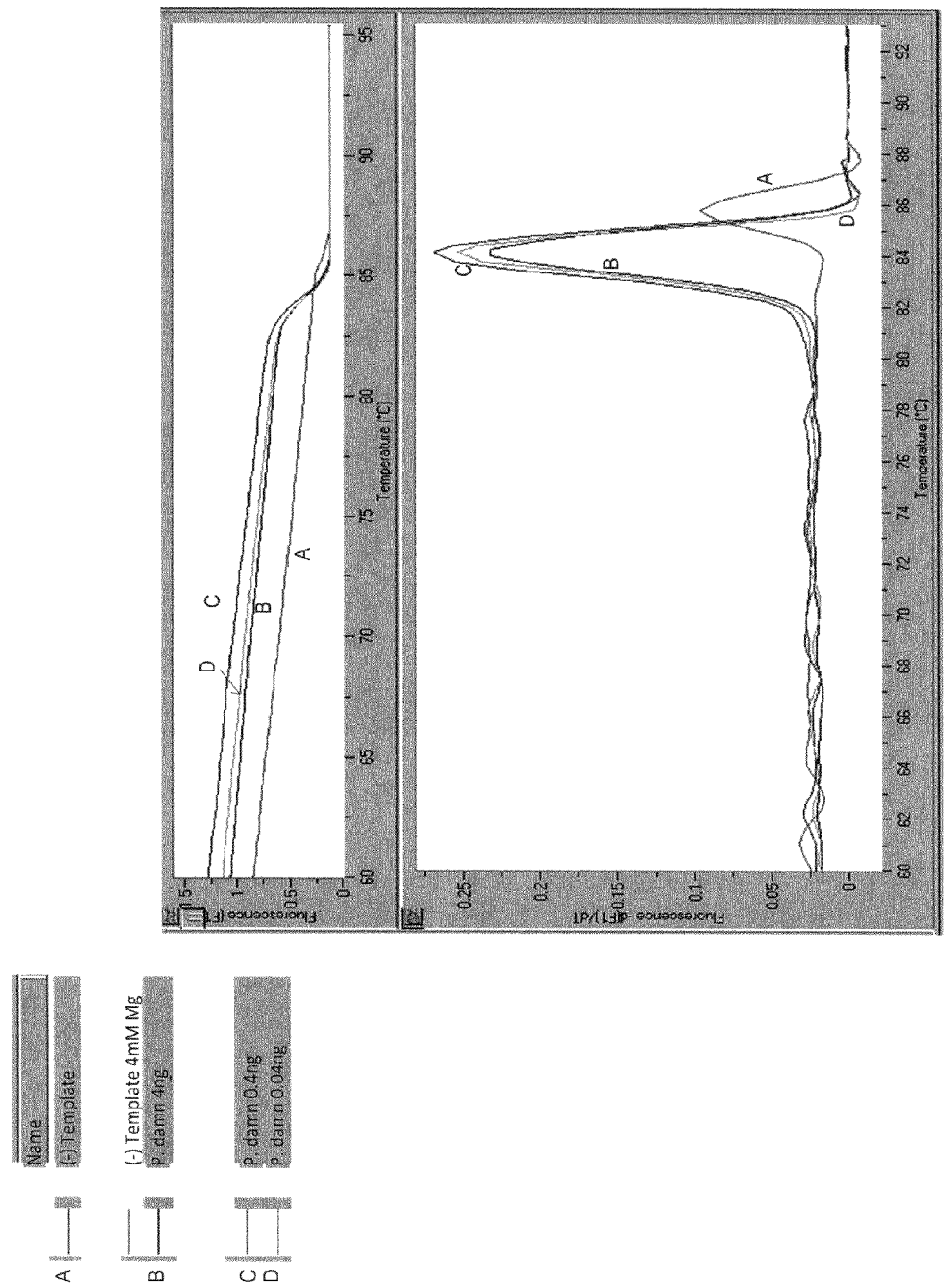
FIG. 28 shows the melt-curve analysis of the PCR as shown in FIG. 27.

Initial qPCR experiments with the Ped134F/PedLac266R primer set were conducted using *P. damnosus* gDNA. Amplification was detected by the increase in fluorescence produced when SYBR Green I intercalates with dsDNA product. The plot in FIG. 27 shows the amplification of 10 fold dilutions of *P. damnosus* gDNA ranging from 4 ng ($C_T$=13.74, dark gray) to 40 pg ($C_T$=21.19, light gray). The no template negative control did not yield any detectable amplification until cycle number thirty-five. The melting curve plots for the amplicons are shown in FIG. 28. The *P. damnosus* amplification yields a specific product having a Tm of 83.75° C. The no template control for this experiment yielded a small amount of a specific amplicon having a Tm of 85.75° C.

Figure 29:
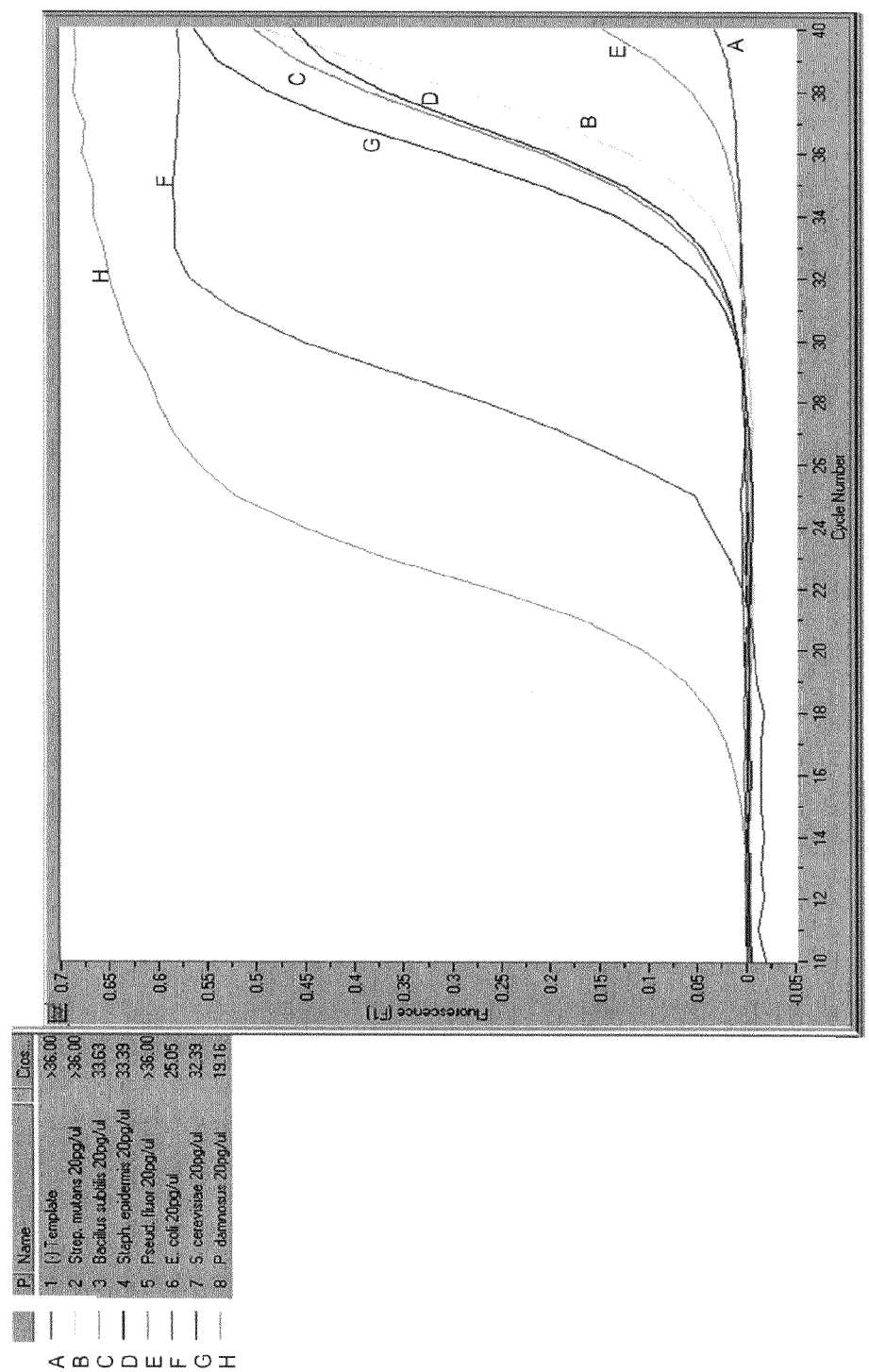
FIG. 29 shows the amplification plot for PCR reactions with Ped134F/PedLac266R primer on various genomic DNA templates.

The specificity of the Ped134F/PedLac266R primer set was examined by performing PCR on various genomic DNA templates. The amplification plot for these reactions is shown in FIG. 29. As expected, the *P. damnosus* amplification displayed the best PCR efficiency with a $C_T$=19.16 cycle (light gray). The *E. coli* genomic amplification (blue-green) yielded a low $C_T$ of 25.05 cycles (which signifies that the *P. damnosus* primers were 64 more specific for their own template than for *E. coli*). The PCR efficiency of the remaining samples from best to worst was; *S. cerevisiae* ($C_T$=32.39), *S. epidermis* ($C_T$=33.39), *B. subtilis* ($C_T$=33.63), *S. mutans* ($C_T$→36), and *P. fluorescens* ($C_T$→36). The no template control for this experiment showed virtually no amplification.

What is claimed is:

1. A method for identification of an organism, comprising the steps of:
   a) aligning a set of related sequences, wherein said set of related sequences comprise at least one polynucleotide sequence from said organism;
   b) searching for a segment with low average information content from said set of aligned related sequences;
   c) selecting from said segment one or more sequences with low individual information contents or a portion thereof as oligonucleotides for identification of said organism; and
   d) hybridizing said oligonucleotides with at least one DNA molecule obtained from said organism,
   wherein the average information content is determined by calculating and comparing the values of $R_{sequence}$ for every equal-length window on said aligned sequences.

2. The method of claim 1, wherein the search for the segment with low average information content is by locating high and low average information content sequence windows along the entire length of said polynucleotide molecule.

3. The method of claim 2, wherein the length of the sequence window is in the range of 20-25 nucleotides.

4. The method of claim 1, wherein the polynucleotide molecule is a ribosomal DNA molecule.

5. The method of claim 1, wherein the organism is a porcine reproductive and respiratory syndrome virus.

6. The method of claim 1, wherein the organism is an organism which negatively affects the production of ethanol from a biomaterial.

7. The method of claim 1, wherein the organism is an organism which spoils the fermentation process of a beverage.

8. The method of claim 4, further comprising a step of using said oligonucleotide as a primer for amplifying at least one DNA molecule obtained from said organism by at least one reaction selected from polymerase chain reaction and ligase chain reaction.

9. A method for identification of an organism, comprising the steps of:

a) aligning a first polynucleotide sequence known to exist in a first organism with at least one additional related polynucleotide sequence from at least one different organism, said at least one additional related polynucleotide sequence being different from one another and from said first polynucleotide sequence;

b) searching for a window with low average information content on said aligned sequences;

c) selecting from said first polynucleotide sequence at least one segment with low individual information content or a portion thereof as an oligonucleotide for identification of said first organism; and d) hybridizing said oligonucleotides with at least one DNA molecule obtained from said organism, wherein the average information content is determined by calculating and comparing the values of $R_{sequence}$ for every equal-length window on said aligned sequences.

10. The method of claim 9, wherein the selected segment has an $R_i$ value that is at least one standard deviation below the average information content of sequences within the same window on the aligned polynucleotide sequences demarcated by the boundaries of the selected segment.

11. The method of claim 9, wherein said first organism and said at least one different organism are different type strains belonging to the same species.

12. The method of claim 9, wherein said first organism and said at least one different organism belong to different species.

13. The method of claim 9, wherein all polynucleotide sequences are DNA sequences.

14. The method of claim 13, further comprising a step of hybridizing said oligonucleotide with at least one DNA molecule obtained from said first organism.

15. The method of claim 13, further comprising a step of using said oligonucleotide as a primer for amplifying at least one DNA molecule obtained from said first organism by using a reaction selected from the group consisting of polymerase chain reaction and ligase chain reaction.

16. A method for identification of a type strain, comprising the steps of:

a) aligning a first polynucleotide sequence known to exist in a first type strain with at least one additional polynucleotide sequence from at least one different type strain, wherein said at least one additional polynucleotide sequence is different from one another and from said first polynucleotide sequence, and said first type strain and said at least one different type strain belong to the same species;

b) searching for a window with low average information content on said aligned sequences; and c) selecting from said first polynucleotide sequence at least one segment with low individual information content or a portion thereof as an oligonucleotide for identification of said first type strain.

17. The method of claim 16, wherein said first type strain and said at least one different type strain are type strains of a porcine reproductive and respiratory syndrome virus.

18. A method for identification of an organism, comprising the steps of:

a) aligning a first polynucleotide sequence known to exist in a first organism with at least one additional related polynucleotide sequence from at least one different organism, said at least one additional polynucleotide sequence being different from one another and from said first polynucleotide sequence;

b) searching for a window with low average information content on said aligned sequences, wherein the average information content is determined by calculating and comparing the values of $R_{sequence}$ for every equal-length segment in the aligned sequences; and c) selecting from said first polynucleotide sequence at least one segment with low individual information content or a portion thereof as an oligonucleotide for identification of said first organism.

19. The method of claim 16, further comprising a step of using said oligonucleotide as a primer for amplifying at least one DNA molecule obtained from said first strain by using a reaction selected from the group consisting of polymerase chain reaction and ligase chain reaction.

20. The method of claim 18, further comprising a step of using said oligonucleotide as a primer for amplifying at least one DNA molecule obtained from said first organism by using a reaction selected from the group consisting of polymerase chain reaction and ligase chain reaction.

* * * * *

SEQUENCE LISTING

```
<160> NUMBER OF SEQ ID NOS: 42

<210> SEQ ID NO 1
<211> LENGTH: 23
<212> TYPE: DNA
<213> ORGANISM: Porcine reproductive and respiratory syndrome virus

<400> SEQUENCE: 1
aacagcggct caaatttaca gct                                              23

<210> SEQ ID NO 2
<211> LENGTH: 23
<212> TYPE: DNA
<213> ORGANISM: Porcine reproductive and respiratory syndrome virus

<400> SEQUENCE: 2
aacagcagct cccaattgca gtc                                              23

<210> SEQ ID NO 3
<211> LENGTH: 23
<212> TYPE: DNA
<213> ORGANISM: Porcine reproductive and respiratory syndrome virus

<400> SEQUENCE: 3
gacagcagct cccatctaca gct                                              23
```

```
<210> SEQ ID NO 4
<211> LENGTH: 23
<212> TYPE: DNA
<213> ORGANISM: Porcine reproductive and respiratory syndrome virus

<400> SEQUENCE: 4
aacaacagct cccatctaca gct                                          23

<210> SEQ ID NO 5
<211> LENGTH: 23
<212> TYPE: DNA
<213> ORGANISM: Porcine reproductive and respiratory syndrome virus

<400> SEQUENCE: 5
agcagcagct ctcattttca gtt                                          23

<210> SEQ ID NO 6
<211> LENGTH: 23
<212> TYPE: DNA
<213> ORGANISM: Porcine reproductive and respiratory syndrome virus

<400> SEQUENCE: 6
acgctctgtt tttggtttcc act                                          23

<210> SEQ ID NO 7
<211> LENGTH: 23
<212> TYPE: DNA
<213> ORGANISM: Porcine reproductive and respiratory syndrome virus

<400> SEQUENCE: 7
aacagcagct ctcattttca gtt                                          23

<210> SEQ ID NO 8
<211> LENGTH: 23
<212> TYPE: DNA
<213> ORGANISM: Porcine reproductive and respiratory syndrome virus

<400> SEQUENCE: 8
acgctatgtt tttggtttcc att                                          23

<210> SEQ ID NO 9
<211> LENGTH: 23
<212> TYPE: DNA
<213> ORGANISM: Porcine reproductive and respiratory syndrome virus

<400> SEQUENCE: 9
acgctatgct tttggtttcc att                                          23

<210> SEQ ID NO 10
<211> LENGTH: 22
<212> TYPE: DNA
<213> ORGANISM: Lactobacillus acidophilus

<400> SEQUENCE: 10
tgacgttggg aaacgctagc gg                                           22

<210> SEQ ID NO 11
<211> LENGTH: 19
<212> TYPE: DNA
<213> ORGANISM: Lactobacillus acidophilus

<400> SEQUENCE: 11
tgacgttggg aaacgctag                                               19
```

```
<210> SEQ ID NO 12
<211> LENGTH: 19
<212> TYPE: DNA
<213> ORGANISM: Lactobacillus acidophilus

<400> SEQUENCE: 12
gacgttggga aacgctagc                                                19

<210> SEQ ID NO 13
<211> LENGTH: 19
<212> TYPE: DNA
<213> ORGANISM: Lactobacillus acidophilus

<400> SEQUENCE: 13
ctagcgtttc ccaacgtca                                                19

<210> SEQ ID NO 14
<211> LENGTH: 23
<212> TYPE: DNA
<213> ORGANISM: Lactobacillus brevis

<400> SEQUENCE: 14
caaaatccgc atggattttg ttt                                           23

<210> SEQ ID NO 15
<211> LENGTH: 20
<212> TYPE: DNA
<213> ORGANISM: Lactobacillus brevis

<400> SEQUENCE: 15
aaaatccgca tggattttgt                                               20

<210> SEQ ID NO 16
<211> LENGTH: 20
<212> TYPE: DNA
<213> ORGANISM: Lactobacillus brevis

<400> SEQUENCE: 16
aaatccgcat ggattttgtt                                               20

<210> SEQ ID NO 17
<211> LENGTH: 20
<212> TYPE: DNA
<213> ORGANISM: Lactobacillus brevis

<400> SEQUENCE: 17
aaacaaaatc catgcggatt                                               20

<210> SEQ ID NO 18
<211> LENGTH: 20
<212> TYPE: DNA
<213> ORGANISM: Lactobacillus brevis

<400> SEQUENCE: 18
tcccgcggcg tattagttag                                               20

<210> SEQ ID NO 19
<211> LENGTH: 19
<212> TYPE: DNA
<213> ORGANISM: Lactobacillus brevis

<400> SEQUENCE: 19
cccgcggcgt attagttag                                                19
```

```
<210> SEQ ID NO 20
<211> LENGTH: 20
<212> TYPE: DNA
<213> ORGANISM: Lactobacillus brevis

<400> SEQUENCE: 20
ctaactaata cgccgcggga                                               20

<210> SEQ ID NO 21
<211> LENGTH: 19
<212> TYPE: DNA
<213> ORGANISM: Lactobacillus brevis

<400> SEQUENCE: 21
ctaactaata cgccgcggg                                                19

<210> SEQ ID NO 22
<211> LENGTH: 23
<212> TYPE: DNA
<213> ORGANISM: Pediococcus damnosus

<400> SEQUENCE: 22
tctggtcttg taactgacgc tga                                           23

<210> SEQ ID NO 23
<211> LENGTH: 20
<212> TYPE: DNA
<213> ORGANISM: Pediococcus damnosus

<400> SEQUENCE: 23
tggtcttgta actgacgctg                                               20

<210> SEQ ID NO 24
<211> LENGTH: 20
<212> TYPE: DNA
<213> ORGANISM: Pediococcus damnosus

<400> SEQUENCE: 24
cgtcttgtaa ctgacgctga                                               20

<210> SEQ ID NO 25
<211> LENGTH: 20
<212> TYPE: DNA
<213> ORGANISM: Pediococcus damnosus

<400> SEQUENCE: 25
tcagcgtcag ttacaagacc                                               20

<210> SEQ ID NO 26
<211> LENGTH: 23
<212> TYPE: DNA
<213> ORGANISM: Pediococcus parvulus

<400> SEQUENCE: 26
ctataaagtg agtggcgaac ggg                                           23

<210> SEQ ID NO 27
<211> LENGTH: 20
<212> TYPE: DNA
<213> ORGANISM: Pediococcus parvulus

<400> SEQUENCE: 27
tataaagtga gtggcgaacg                                               20
```

-continued

<210> SEQ ID NO 28
<211> LENGTH: 20
<212> TYPE: DNA
<213> ORGANISM: Pediococcus parvulus

<400> SEQUENCE: 28
ataaagtgag tggcgaacgg                                        20

<210> SEQ ID NO 29
<211> LENGTH: 19
<212> TYPE: DNA
<213> ORGANISM: Pediococcus parvulus

<400> SEQUENCE: 29
ctataaagtg agtggcgaa                                         19

<210> SEQ ID NO 30
<211> LENGTH: 20
<212> TYPE: DNA
<213> ORGANISM: Pediococcus parvulus

<400> SEQUENCE: 30
ccgttcgcca ctcactttat                                        20

<210> SEQ ID NO 31
<211> LENGTH: 21
<212> TYPE: DNA
<213> ORGANISM: Saccharomyces cerevisiae

<400> SEQUENCE: 31
ccaacatttt cgtatatggc g                                      21

<210> SEQ ID NO 32
<211> LENGTH: 22
<212> TYPE: DNA
<213> ORGANISM: Saccharomyces cerevisiae

<400> SEQUENCE: 32 tccaacalttt aggaaaaaac gc                                    22

<210> SEQ ID NO 33
<211> LENGTH: 20
<212> TYPE: DNA
<213> ORGANISM: Artificial
<220> FEATURE:
<223> OTHER INFORMATION: Synthetic oligonucleotide

<400> SEQUENCE: 33
yayraagtga gtggcgaacg                                        20

<210> SEQ ID NO 34
<211> LENGTH: 21
<212> TYPE: DNA
<213> ORGANISM: Artificial
<220> FEATURE:
<223> OTHER INFORMATION: Synthetic oligonucleotide

<400> SEQUENCE: 34
ggwycatcca gaagygatag c                                      21

<210> SEQ ID NO 35
<211> LENGTH: 21
<212> TYPE: DNA
<213> ORGANISM: Artificial

```
<220> FEATURE:
<223> OTHER INFORMATION: Synthetic oligonucleotide

<400> SEQUENCE: 35
ggtccatcca gaagygatag c                                              21

<210> SEQ ID NO 36
<211> LENGTH: 21
<212> TYPE: DNA
<213> ORGANISM: Artificial
<220> FEATURE:
<223> OTHER INFORMATION: Synthetic oligonucleotide

<400> SEQUENCE: 36
gctatcrctt ctggatgrwc c                                              21

<210> SEQ ID NO 37
<211> LENGTH: 21
<212> TYPE: DNA
<213> ORGANISM: Artificial
<220> FEATURE:
<223> OTHER INFORMATION: Synthetic oligonucleotide

<400> SEQUENCE: 37
gctatcrctt ctggatggac c                                              21

<210> SEQ ID NO 38
<211> LENGTH: 18
<212> TYPE: DNA
<213> ORGANISM: Artificial
<220> FEATURE:
<223> OTHER INFORMATION: Synthetic oligonucleotide

<400> SEQUENCE: 38
ccagtttccg atgcactt                                                  18

<210> SEQ ID NO 39
<211> LENGTH: 18
<212> TYPE: DNA
<213> ORGANISM: Artificial
<220> FEATURE:
<223> OTHER INFORMATION: Synthetic oligonucleotide

<400> SEQUENCE: 39
aagtgcatcg gaaactgg                                                  18

<210> SEQ ID NO 40
<211> LENGTH: 19
<212> TYPE: DNA
<213> ORGANISM: Artificial
<220> FEATURE:
<223> OTHER INFORMATION: Synthetic oligonucleotide

<400> SEQUENCE: 40
ccctaatcat ctgtcccac                                                 19

<210> SEQ ID NO 41
<211> LENGTH: 20
<212> TYPE: DNA
<213> ORGANISM: Artificial
<220> FEATURE:
<223> OTHER INFORMATION: Synthetic oligonucleotide

<400> SEQUENCE: 41
gtgcaatccg tagagatacg                                                20
```

```
<210> SEQ ID NO 42
<211> LENGTH: 19
<212> TYPE: DNA
<213> ORGANISM: Artificial
<220> FEATURE:
<223> OTHER INFORMATION: Synthetic oligonucleotide

<400> SEQUENCE: 42
ccacctgtct tagtgtccc                                                    19
```